United States Patent
Thomas et al.

(10) Patent No.: US 8,252,229 B2
(45) Date of Patent: Aug. 28, 2012

(54) METHOD AND SYSTEM FOR STERILIZING AN ANALYTE SENSOR

(75) Inventors: Christopher Allen Thomas, San Leandro, CA (US); Jasmin Y. Zhao, Alameda, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 668 days.

(21) Appl. No.: 12/422,223

(22) Filed: Apr. 10, 2009

(65) Prior Publication Data

US 2009/0257911 A1 Oct. 15, 2009

Related U.S. Application Data

(60) Provisional application No. 61/044,017, filed on Apr. 10, 2008.

(51) Int. Cl.
| | |
|---|---|
| A61L 2/00 | (2006.01) |
| G01N 21/00 | (2006.01) |
| A61N 5/00 | (2006.01) |
| C12Q 1/00 | (2006.01) |
| C12N 13/00 | (2006.01) |
| A61B 5/05 | (2006.01) |
| A61B 1/00 | (2006.01) |

(52) U.S. Cl. ...... 422/22; 422/1; 250/453.11; 250/492.1; 600/347; 600/365; 600/133; 435/4; 435/173.1

(58) Field of Classification Search ............... 422/1, 22; 250/453.11, 492.1; 600/347, 365, 133; 435/4, 435/173.1
See application file for complete search history.

(56) References Cited

U.S. PATENT DOCUMENTS

| | | | |
|---|---|---|---|
| 3,581,062 A | 5/1971 | Aston | |
| 3,926,760 A | 12/1975 | Allen et al. | |
| 3,949,388 A | 4/1976 | Fuller | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,425,920 A | 1/1984 | Bourland et al. | |
| 4,478,976 A | 10/1984 | Goertz et al. | |
| 4,494,950 A | 1/1985 | Fischell | |
| 4,509,531 A | 4/1985 | Ward | |

(Continued)

FOREIGN PATENT DOCUMENTS

DE 4401400 7/1995

(Continued)

OTHER PUBLICATIONS

International Search Report and Written Opinion of the International Searching Authority for PCT Application No. PCT/US2009/040285 filed Apr. 10, 2009, mailed May 29, 2009.

(Continued)

*Primary Examiner* — Jill Warden
*Assistant Examiner* — Monzer Chorbaji
(74) *Attorney, Agent, or Firm* — Jackson & Co., LLP

(57) ABSTRACT

In one aspect, there is provided assembling an analyte sensor with an analyte sensor insertion device, packaging the assembled analyte sensor and sensor insertion device in a substantially airtight seal, and irradiating the packaged assembled analyte sensor and sensor insertion device at a predetermined dose using one or more electron beam accelerators.

28 Claims, 13 Drawing Sheets

U.S. PATENT DOCUMENTS

| | | |
|---|---|---|
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,854,322 A | 8/1989 | Ash et al. |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,431,160 A | 7/1995 | Wilkins |
| 5,431,921 A | 7/1995 | Thombre |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,653,239 A | 8/1997 | Pompei et al. |
| 5,665,222 A | 9/1997 | Heller et al. |
| 5,711,001 A | 1/1998 | Bussan et al. |
| 5,711,861 A | 1/1998 | Ward et al. |
| 5,735,285 A | 4/1998 | Albert et al. |
| 5,772,586 A | 6/1998 | Heinonen et al. |
| 5,791,344 A | 8/1998 | Schulman et al. |
| 5,899,855 A | 5/1999 | Brown |
| 5,925,021 A | 7/1999 | Castellano et al. |
| 5,942,979 A | 8/1999 | Luppino |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,049,727 A | 4/2000 | Crothall |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,348,640 B1 | 2/2002 | Navot et al. |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,478,736 B1 | 11/2002 | Mault |
| 6,484,045 B1 | 11/2002 | Holker et al. |
| 6,484,046 B1 | 11/2002 | Say et al. |
| 6,497,655 B1 | 12/2002 | Linberg et al. |
| 6,514,689 B2 | 2/2003 | Han et al. |
| 6,514,718 B2 | 2/2003 | Heller et al. |
| 6,522,927 B1 | 2/2003 | Bishay et al. |
| 6,549,796 B2 | 4/2003 | Sohrab |
| 6,551,494 B1 | 4/2003 | Heller et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,645,359 B1 | 11/2003 | Bhullar et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,662,439 B1 | 12/2003 | Bhullar |
| 6,668,196 B1 | 12/2003 | Villegas et al. |
| 6,687,546 B2 | 2/2004 | Lebel et al. |

| | | | | | | |
|---|---|---|---|---|---|---|
| 6,689,056 | B1 | 2/2004 | Kilcoyne et al. | 7,384,397 | B2 | 6/2008 | Zhang et al. |
| 6,694,191 | B2 | 2/2004 | Starkweather et al. | 7,386,937 | B2 | 6/2008 | Bhullar et al. |
| 6,695,860 | B1 | 2/2004 | Ward et al. | 7,424,318 | B2 | 9/2008 | Brister et al. |
| 6,702,857 | B2 | 3/2004 | Brauker et al. | 7,460,898 | B2 | 12/2008 | Brister et al. |
| 6,733,446 | B2 | 5/2004 | Lebel et al. | 7,467,003 | B2 | 12/2008 | Brister et al. |
| 6,740,075 | B2 | 5/2004 | Lebel et al. | 7,471,972 | B2 | 12/2008 | Rhodes et al. |
| 6,741,877 | B1 | 5/2004 | Shults et al. | 7,494,465 | B2 | 2/2009 | Brister et al. |
| 6,746,582 | B2 | 6/2004 | Heller et al. | 7,497,827 | B2 | 3/2009 | Brister et al. |
| 6,758,810 | B2 | 7/2004 | Lebel et al. | 7,519,408 | B2 | 4/2009 | Rasdal et al. |
| 6,767,440 | B1 | 7/2004 | Bhullar et al. | 7,565,197 | B2 | 7/2009 | Haubrich et al. |
| 6,770,030 | B1 | 8/2004 | Schaupp et al. | 7,574,266 | B2 | 8/2009 | Dudding et al. |
| 6,790,178 | B1 | 9/2004 | Mault et al. | 7,583,990 | B2 | 9/2009 | Goode, Jr. et al. |
| 6,804,558 | B2 | 10/2004 | Haller et al. | 7,591,801 | B2 | 9/2009 | Brauker et al. |
| 6,809,653 | B1 | 10/2004 | Mann et al. | 7,599,726 | B2 | 10/2009 | Goode, Jr. et al. |
| 6,810,290 | B2 | 10/2004 | Lebel et al. | 7,602,310 | B2 | 10/2009 | Mann et al. |
| 6,811,533 | B2 | 11/2004 | Lebel et al. | 7,613,491 | B2 | 11/2009 | Boock et al. |
| 6,811,534 | B2 | 11/2004 | Bowman, IV et al. | 7,615,007 | B2 | 11/2009 | Shults et al. |
| 6,813,519 | B2 | 11/2004 | Lebel et al. | 7,632,228 | B2 | 12/2009 | Brauker et al. |
| 6,862,465 | B2 | 3/2005 | Shults et al. | 7,637,868 | B2 | 12/2009 | Saint et al. |
| 6,873,268 | B2 | 3/2005 | Lebel et al. | 7,640,048 | B2 | 12/2009 | Dobbles et al. |
| 6,878,112 | B2 | 4/2005 | Linberg et al. | 7,651,596 | B2 | 1/2010 | Petisce et al. |
| 6,881,551 | B2 | 4/2005 | Heller et al. | 7,654,956 | B2 | 2/2010 | Brister et al. |
| 6,892,085 | B2 | 5/2005 | McIvor et al. | 7,657,297 | B2 | 2/2010 | Simpson et al. |
| 6,895,265 | B2 | 5/2005 | Silver | 7,711,402 | B2 | 5/2010 | Shults et al. |
| 6,931,327 | B2 | 8/2005 | Goode, Jr. et al. | 7,713,574 | B2 | 5/2010 | Brister et al. |
| 6,932,894 | B2 | 8/2005 | Mao et al. | 7,715,893 | B2 | 5/2010 | Kamath et al. |
| 6,936,006 | B2 | 8/2005 | Sabra | 2002/0019022 | A1 | 2/2002 | Dunn et al. |
| 6,942,518 | B2 | 9/2005 | Liamos et al. | 2002/0042090 | A1 | 4/2002 | Heller et al. |
| 6,950,708 | B2 | 9/2005 | Bowman, IV et al. | 2002/0050250 | A1 | 5/2002 | Peterson et al. |
| 6,958,705 | B2 | 10/2005 | Lebel et al. | 2002/0103499 | A1 | 8/2002 | Perez et al. |
| 6,968,294 | B2 | 11/2005 | Gutta et al. | 2002/0106709 | A1 | 8/2002 | Potts et al. |
| 6,971,274 | B2 | 12/2005 | Olin | 2002/0128594 | A1 | 9/2002 | Das et al. |
| 6,973,706 | B2 | 12/2005 | Say et al. | 2002/0161288 | A1 | 10/2002 | Shin et al. |
| 6,974,437 | B2 | 12/2005 | Lebel et al. | 2002/0164836 | A1 | 11/2002 | Ho |
| 6,983,867 | B1 | 1/2006 | Fugere | 2003/0023317 | A1 | 1/2003 | Brauker et al. |
| 6,990,366 | B2 | 1/2006 | Say et al. | 2003/0023461 | A1 | 1/2003 | Quintanilla et al. |
| 6,997,907 | B2 | 2/2006 | Safabash et al. | 2003/0032867 | A1 | 2/2003 | Crothall et al. |
| 6,998,247 | B2 | 2/2006 | Monfre et al. | 2003/0032874 | A1 | 2/2003 | Rhodes et al. |
| 7,003,336 | B2 | 2/2006 | Holker et al. | 2003/0042137 | A1 | 3/2003 | Mao et al. |
| 7,003,340 | B2 | 2/2006 | Say et al. | 2003/0065308 | A1 | 4/2003 | Lebel et al. |
| 7,003,341 | B2 | 2/2006 | Say et al. | 2003/0078481 | A1* | 4/2003 | McIvor et al. ................ 600/347 |
| 7,024,245 | B2 | 4/2006 | Lebel et al. | 2003/0134347 | A1 | 7/2003 | Heller et al. |
| 7,041,068 | B2 | 5/2006 | Freeman et al. | 2003/0168338 | A1 | 9/2003 | Gao et al. |
| 7,041,468 | B2 | 5/2006 | Drucker et al. | 2003/0176933 | A1 | 9/2003 | Lebel et al. |
| 7,052,483 | B2 | 5/2006 | Wojcik | 2003/0187338 | A1 | 10/2003 | Say et al. |
| 7,056,302 | B2 | 6/2006 | Douglas | 2003/0188427 | A1 | 10/2003 | Say et al. |
| 7,058,453 | B2 | 6/2006 | Nelson et al. | 2003/0199790 | A1 | 10/2003 | Boecker et al. |
| 7,060,031 | B2 | 6/2006 | Webb et al. | 2003/0212379 | A1 | 11/2003 | Bylund et al. |
| 7,073,246 | B2 | 7/2006 | Bhullar et al. | 2003/0217966 | A1 | 11/2003 | Tapsak et al. |
| 7,074,307 | B2 | 7/2006 | Simpson et al. | 2004/0010207 | A1 | 1/2004 | Flaherty et al. |
| 7,081,195 | B2 | 7/2006 | Simpson et al. | 2004/0011671 | A1 | 1/2004 | Shults et al. |
| 7,098,803 | B2 | 8/2006 | Mann et al. | 2004/0040840 | A1 | 3/2004 | Mao et al. |
| 7,108,778 | B2 | 9/2006 | Simpson et al. | 2004/0045879 | A1 | 3/2004 | Shults et al. |
| 7,110,803 | B2 | 9/2006 | Shults et al. | 2004/0054263 | A1 | 3/2004 | Moerman et al. |
| 7,113,821 | B1 | 9/2006 | Sun et al. | 2004/0064068 | A1 | 4/2004 | DeNuzzio et al. |
| 7,118,667 | B2 | 10/2006 | Lee | 2004/0106858 | A1 | 6/2004 | Say et al. |
| 7,125,382 | B2 | 10/2006 | Zhou et al. | 2004/0122353 | A1 | 6/2004 | Shahmirian et al. |
| 7,134,999 | B2 | 11/2006 | Brauker et al. | 2004/0133164 | A1 | 7/2004 | Funderburk et al. |
| 7,136,689 | B2 | 11/2006 | Shults et al. | 2004/0135684 | A1 | 7/2004 | Steinthal et al. |
| 7,171,274 | B2 | 1/2007 | Starkweather et al. | 2004/0138588 | A1 | 7/2004 | Saikley et al. |
| 7,190,988 | B2 | 3/2007 | Say et al. | 2004/0152622 | A1 | 8/2004 | Keith et al. |
| 7,192,450 | B2 | 3/2007 | Brauker et al. | 2004/0167801 | A1 | 8/2004 | Say et al. |
| 7,198,606 | B2 | 4/2007 | Boecker et al. | 2004/0171921 | A1 | 9/2004 | Say et al. |
| 7,225,535 | B2 | 6/2007 | Feldman et al. | 2004/0176672 | A1 | 9/2004 | Silver et al. |
| 7,226,978 | B2 | 6/2007 | Tapsak et al. | 2004/0186362 | A1 | 9/2004 | Brauker et al. |
| 7,267,665 | B2 | 9/2007 | Steil et al. | 2004/0186365 | A1 | 9/2004 | Jin et al. |
| 7,276,029 | B2 | 10/2007 | Goode, Jr. et al. | 2004/0193090 | A1 | 9/2004 | Lebel et al. |
| 7,276,146 | B2 | 10/2007 | Wilsey | 2004/0199059 | A1 | 10/2004 | Brauker et al. |
| 7,276,147 | B2 | 10/2007 | Wilsey | 2004/0204687 | A1 | 10/2004 | Mogensen et al. |
| 7,278,983 | B2 | 10/2007 | Ireland et al. | 2004/0206625 | A1 | 10/2004 | Bhullar et al. |
| 7,287,318 | B2 | 10/2007 | Bhullar et al. | 2004/0206916 | A1 | 10/2004 | Colvin, Jr. et al. |
| 7,291,497 | B2 | 11/2007 | Holmes et al. | 2004/0225338 | A1 | 11/2004 | Lebel et al. |
| 7,299,082 | B2 | 11/2007 | Feldman et al. | 2004/0236200 | A1 | 11/2004 | Say et al. |
| 7,310,544 | B2 | 12/2007 | Brister et al. | 2004/0254433 | A1 | 12/2004 | Bandis et al. |
| 7,335,294 | B2 | 2/2008 | Heller et al. | 2004/0254434 | A1 | 12/2004 | Goodnow et al. |
| 7,354,420 | B2 | 4/2008 | Steil et al. | 2004/0267300 | A1 | 12/2004 | Mace |
| 7,364,592 | B2 | 4/2008 | Carr-Brendel et al. | 2005/0003470 | A1 | 1/2005 | Nelson et al. |
| 7,366,556 | B2 | 4/2008 | Brister et al. | 2005/0004494 | A1 | 1/2005 | Perez et al. |
| 7,379,765 | B2 | 5/2008 | Petisce et al. | 2005/0010269 | A1 | 1/2005 | Lebel et al. |

| Publication No. | Date | Inventor |
|---|---|---|
| 2005/0027177 A1 | 2/2005 | Shin et al. |
| 2005/0027463 A1 | 2/2005 | Goode, Jr. et al. |
| 2005/0031689 A1 | 2/2005 | Shults et al. |
| 2005/0043598 A1 | 2/2005 | Goode, Jr. et al. |
| 2005/0090607 A1 | 4/2005 | Tapsak et al. |
| 2005/0103624 A1 | 5/2005 | Bhullar et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0277164 A1 | 12/2005 | Drucker et al. |
| 2005/0284758 A1 | 12/2005 | Funke et al. |
| 2005/0287620 A1 | 12/2005 | Heller et al. |
| 2006/0001538 A1 | 1/2006 | Kraft et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0042080 A1 | 3/2006 | Say et al. |
| 2006/0049359 A1* | 3/2006 | Busta et al. ............... 250/370.09 |
| 2006/0166629 A1 | 7/2006 | Reggiardo |
| 2006/0173444 A1 | 8/2006 | Choy et al. |
| 2006/0189863 A1 | 8/2006 | Heller et al. |
| 2006/0200981 A1 | 9/2006 | Bhullar et al. |
| 2006/0200982 A1 | 9/2006 | Bhullar et al. |
| 2006/0222566 A1 | 10/2006 | Brauker et al. |
| 2006/0226985 A1 | 10/2006 | Goodnow et al. |
| 2006/0247508 A1 | 11/2006 | Fennell |
| 2006/0247710 A1 | 11/2006 | Goetz et al. |
| 2006/0253085 A1 | 11/2006 | Geismar et al. |
| 2006/0253086 A1 | 11/2006 | Moberg et al. |
| 2006/0264888 A1 | 11/2006 | Moberg et al. |
| 2006/0270922 A1 | 11/2006 | Brauker et al. |
| 2006/0287691 A1 | 12/2006 | Drew |
| 2007/0027381 A1 | 2/2007 | Stafford |
| 2007/0060814 A1 | 3/2007 | Stafford |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0106135 A1 | 5/2007 | Sloan et al. |
| 2007/0111196 A1* | 5/2007 | Alarcon et al. .................. 435/4 |
| 2007/0149875 A1 | 6/2007 | Ouyang et al. |
| 2007/0156033 A1 | 7/2007 | Causey, III et al. |
| 2007/0161070 A1 | 7/2007 | Wilsey |
| 2007/0163880 A1 | 7/2007 | Woo et al. |
| 2007/0173706 A1 | 7/2007 | Neinast et al. |
| 2007/0191701 A1 | 8/2007 | Feldman et al. |
| 2007/0197889 A1* | 8/2007 | Brister et al. ................ 600/347 |
| 2007/0203407 A1 | 8/2007 | Hoss et al. |
| 2007/0203966 A1 | 8/2007 | Brauker et al. |
| 2007/0219496 A1 | 9/2007 | Kamen et al. |
| 2007/0222609 A1 | 9/2007 | Duron et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0255531 A1 | 11/2007 | Drew |
| 2007/0258395 A1 | 11/2007 | Jollota et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0064943 A1 | 3/2008 | Talbot et al. |
| 2008/0071156 A1 | 3/2008 | Brister et al. |
| 2008/0071328 A1 | 3/2008 | Haubrich et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0108942 A1 | 5/2008 | Brister et al. |
| 2008/0119705 A1 | 5/2008 | Patel et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0235469 A1 | 9/2008 | Drew |
| 2008/0242961 A1 | 10/2008 | Brister et al. |
| 2008/0255438 A1 | 10/2008 | Saidara et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2009/0005666 A1 | 1/2009 | Shin et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0085768 A1 | 4/2009 | Patel et al. |
| 2009/0099436 A1 | 4/2009 | Brister et al. |

| Publication | Date | Inventor |
|---|---|---|
| 2009/0112478 A1 | 4/2009 | Mueller, Jr. et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |

FOREIGN PATENT DOCUMENTS

| | | |
|---|---|---|
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1430831 | 6/2004 |
| WO | WO-96/25089 | 8/1996 |
| WO | WO-96/35370 | 11/1996 |
| WO | WO-98/04902 | 2/1998 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/061420 | 7/2004 |
| WO | WO-2005/041766 | 5/2005 |
| WO | WO-2005/089103 | 9/2005 |
| WO | WO-2006/015922 | 2/2006 |
| WO | WO-2006/024671 | 3/2006 |
| WO | WO-2006/079114 | 7/2006 |
| WO | WO-2006/118947 | 11/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/031106 | 3/2008 |

OTHER PUBLICATIONS

Armour, J. C., et al., "Application of Chronic Intravascular Blood Glucose Sensor in Dogs", *Diabetes*, vol. 39, 1990, pp. 1519-1526.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Gluose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutanteous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

European Patent Application No. 09729717.0, Supplementary European Search Report mailed Oct. 21, 2011.

PCT Application No. PCT/US2009/040285, International Preliminary Report on Patentability and Written Opinion of the International Searching Authority mailed Oct. 21, 2010.

* cited by examiner

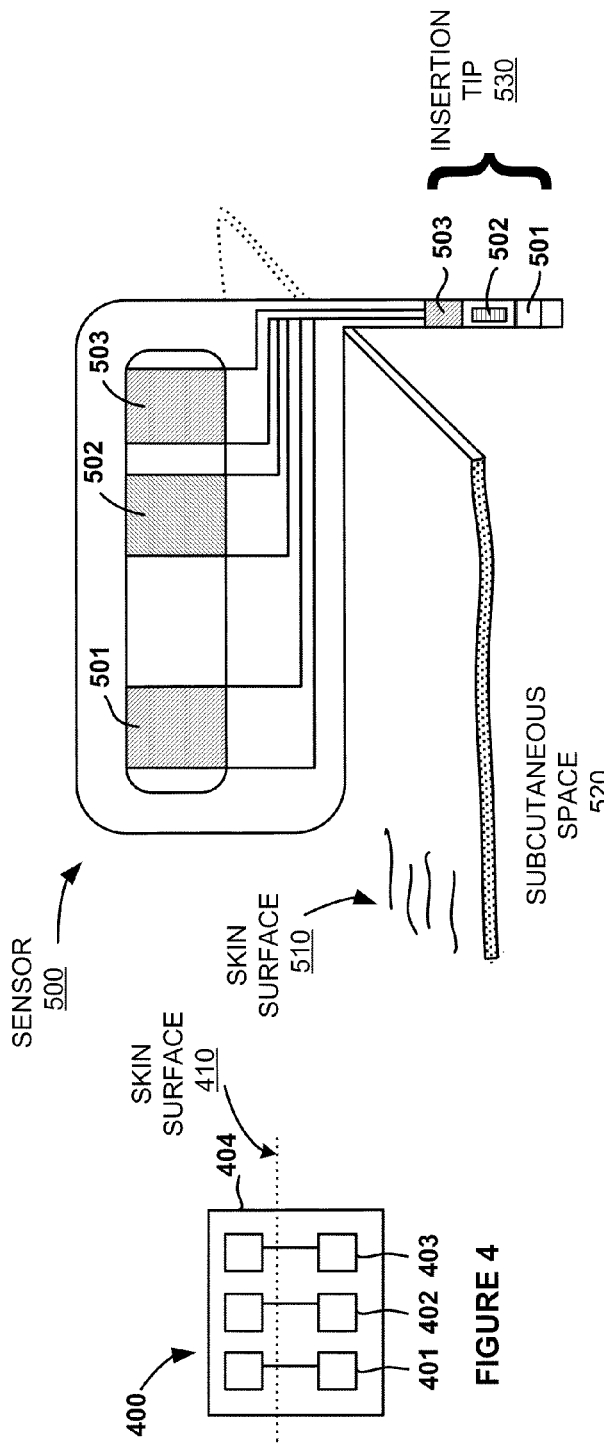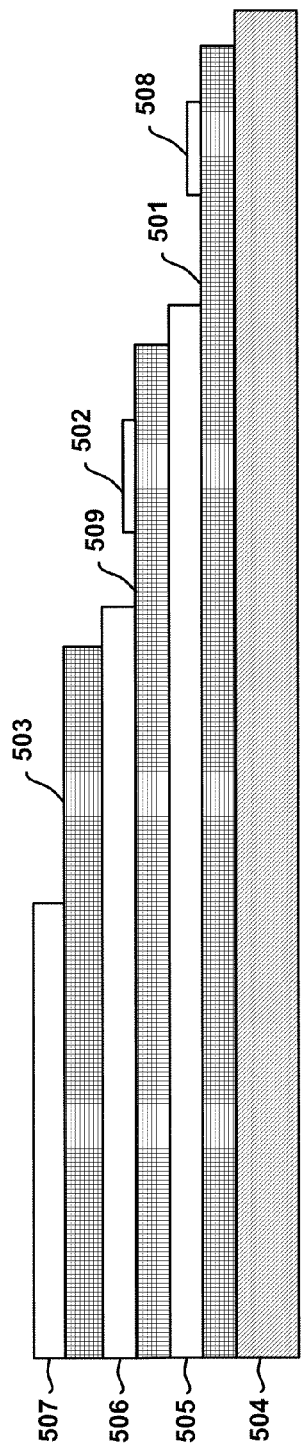

METHOD AND SYSTEM FOR STERILIZING AN ANALYTE SENSOR

RELATED APPLICATIONS

The present application claims priority under 35 U.S.C. §119(e) to U.S. provisional application No. 61/044,017 filed Apr. 10, 2008 entitled "Method and System for Sterilizing an Analyte Sensor," and assigned to the assignee of the present application, Abbott Diabetes Care Inc. of Alameda, Calif., the disclosure of which is incorporated herein by reference for all purposes.

BACKGROUND

The detection of the level of glucose or other analytes, such as lactate, oxygen or the like, in certain individuals is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

Devices have been developed for continuous or automatic monitoring of analytes, such as glucose, in bodily fluid such as in the blood stream or in interstitial fluid. Some of these analyte measuring devices are configured so that at least a portion of the devices are positioned below a skin surface of a user, e.g., in a blood vessel, in the subcutaneous or dermal tissue of a user.

It is important for devices that are to be implanted in the body or positioned below a skin surface of a user, such as in a blood vessel or subcutaneous tissue, to be sterile upon insertion into the user. Sterilization is any number of processes that effectively eliminate or kill transmissible agents, such as bacteria, fungi, and viruses, that may be located on a non-sterile device. These transmittable agents, if not eliminated from the device, may be substantially detrimental to the health and safety of the user.

Existing techniques for sterilization of medical devices, kits or components generally meet several challenges. Whether the sterilization includes the use of chemicals or irradiation of light beams, in order to attain the desired sterility assurance level (SAL), there are considerations that must be accounted for. For example, when a target device or component for sterilization includes different materials having different properties such as metal, plastic, biologics, chemistries, including any combination thereof, the challenges of sterilization can be significant. In addition, when a target device or component is already packaged prior to sterilization, the material comprising the packaging as well as its properties, such as porosity, needs to be considered, further increasing the sterilization challenges.

SUMMARY

In view of the foregoing, provided in accordance with the embodiments of the present disclosure are methods and systems for the sterilization of medical devices, including devices for the continuous or automatic monitoring of analytes, such as glucose, in bodily fluid. In one aspect, there is provided assembling an analyte sensor with an analyte sensor insertion device, packaging the assembled analyte sensor and sensor insertion device in a container which may optionally include a substantially airtight seal, and irradiating the packaged assembled analyte sensor and sensor insertion device at a dose effective to sterilize the package.

In one aspect, the electron beam sterilization of an assembled and packaged analyte sensor and sensor insertion device results in a relatively long term shelf life (for example, approximately 18 months), with controllable moisture content within the packaging, while not adversely impacting the materials of the assembled and packaged sensor and insertion device, for example, including the adhesive component of the device as well as of the packaging.

BRIEF DESCRIPTION OF THE DRAWINGS

FIG. 4 shows a schematic diagram of an embodiment of an analyte sensor according to the present disclosure;

FIGS. 5A-5B show a perspective view and a cross sectional view, respectively of an embodiment the analyte sensor of FIG. 4;

DETAILED DESCRIPTION

Figure 1:
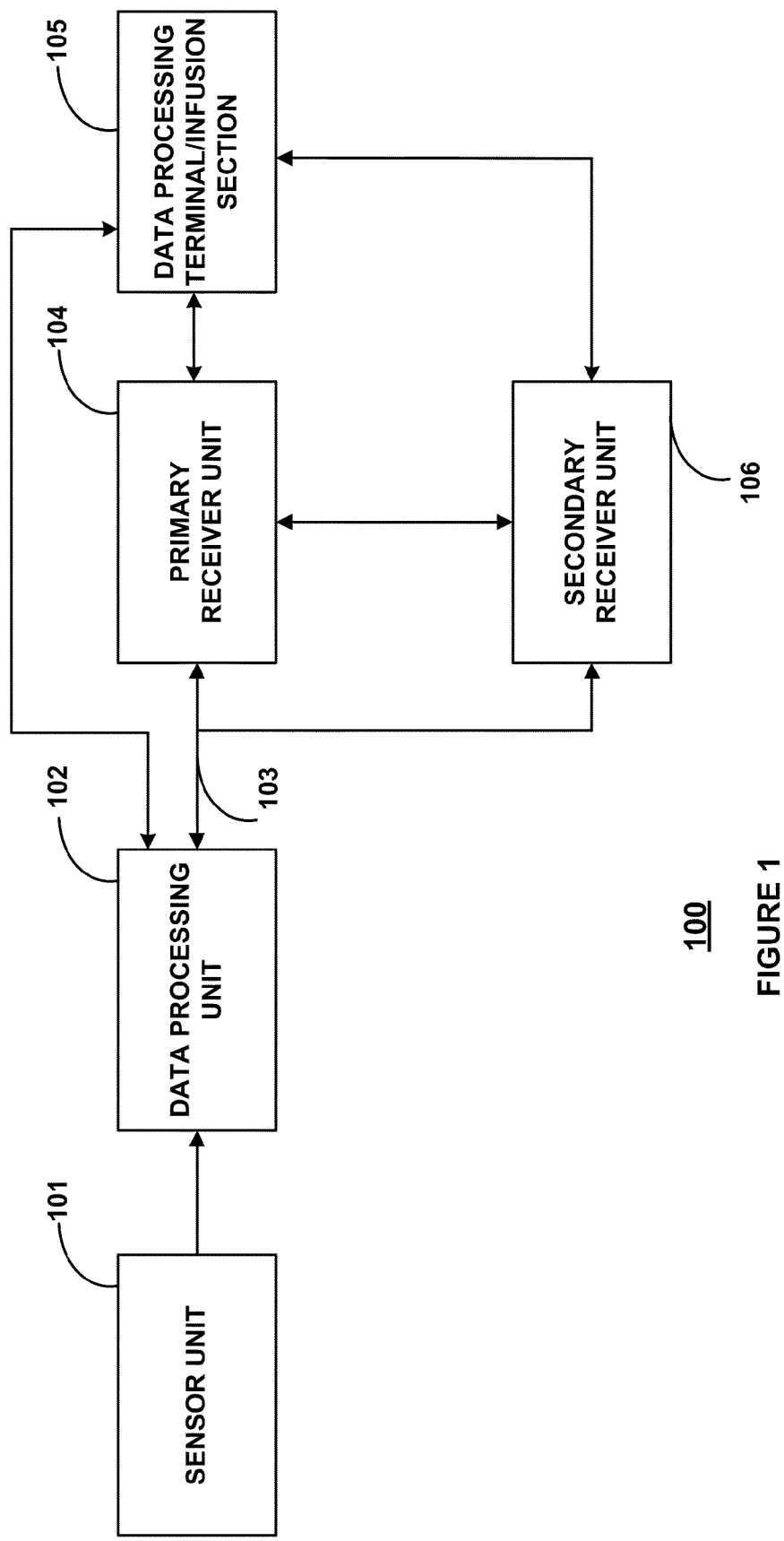
FIG. 1 shows a block diagram of an embodiment of a data monitoring and management system according to the present disclosure.

Before the present disclosure is described, it is to be understood that this invention is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to methods and devices for detecting at least one analyte such as glucose in body fluid. In certain embodiments, the present disclosure relates to the continuous and/or automatic in vivo monitoring of the level of an analyte using an analyte sensor.

Accordingly, embodiments include analyte monitoring devices and systems that include an analyte sensor—at least a portion of which is positionable beneath the skin of the user— for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc. The sensor may be, for example, subcutaneously positionable in a patient for the continuous or periodic monitoring of a level of an analyte in a patient's interstitial fluid. For the purposes of this description, continuous monitoring and periodic monitoring will be used interchangeably, unless noted otherwise. The analyte level may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Analyte sensors may be insertable into a vein, artery, or other portion of the body containing fluid. Embodiments of the analyte sensors of the subject invention may be configured for monitoring the level of the analyte over a time period which may range from minutes, hours, days, weeks, or longer.

Of interest are analyte sensors, such as glucose sensors, that are capable of in vivo detection of an analyte for about one hour or more, e.g., about a few hours or more, e.g., about a few days of more, e.g., about three or more days, e.g., about five days or more, e.g., about seven days or more, e.g., about several weeks or at least one month. Future analyte levels may be predicted based on information obtained, e.g., the current analyte level at time to, the rate of change of the analyte, etc. Predictive alarms may notify the user of predicted analyte levels that may be of concern prior in advance of the analyte level reaching the future level. This enables the user an opportunity to take corrective action.

FIG. 1 shows a data monitoring and management system such as, for example, an analyte (e.g., glucose) monitoring system 100 in accordance with certain embodiments. Embodiments of the subject invention are further described primarily with respect to glucose monitoring devices and systems, and methods of glucose detection, for convenience only and such description is in no way intended to limit the scope of the invention. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 includes a sensor 101, a data processing unit 102 connectable to the sensor 101, and a primary receiver unit 104 which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104, the data processing terminal 105 or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or bi-directional communication device.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit 102 performs data processing functions, where such functions may include but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In one aspect, the primary receiver unit 104 may include an analog interface section including and RF receiver and an antenna that is configured to communicate with the data processing unit 102 via the communication link 103, data processing unit 102 and a data processing section for processing the received data from the data processing unit 102 such as data decoding, error detection and correction, data clock generation, and/or data bit recovery.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone or similar phone), mp3 player, pager, and the like), drug delivery device, each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include an infusion device such as an insulin infusion pump or the like, which may be configured to administer insulin to patients, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user).

In particular embodiments, the data processing terminal 105, which may include an insulin pump, may be configured to receive the analyte signals from the data processing unit 102, and thus, incorporate the functions of the primary receiver unit 104 including data processing for managing the patient's insulin therapy and analyte monitoring. In certain embodiments, the communication link 103 as well as one or more of the other communication interfaces shown in FIG. 1 may use one or more of an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements) while avoiding potential data collision and interference.

Figure 2:
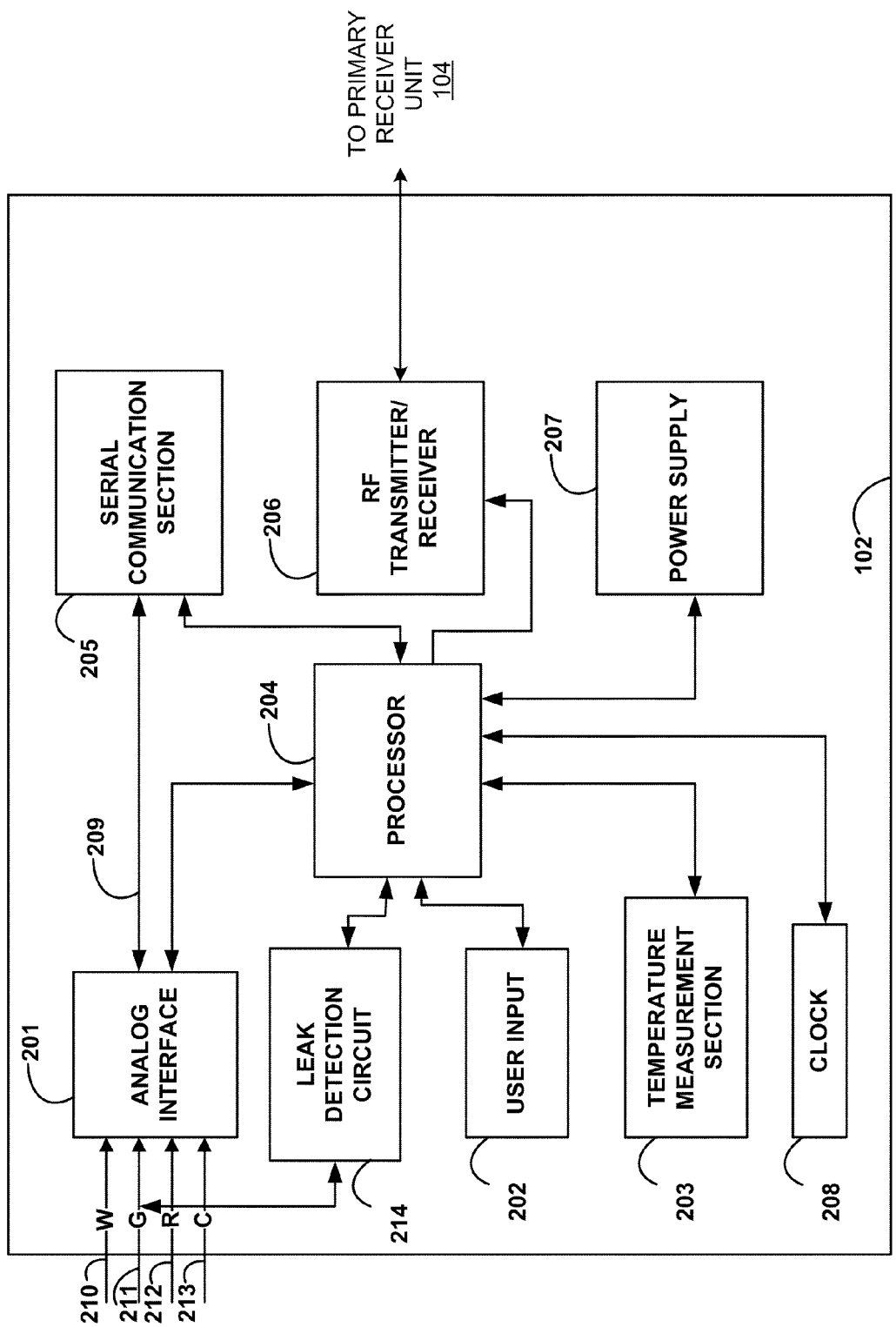
FIG. 2 shows a block diagram of an embodiment of the data processing unit of the data monitoring and management system of FIG. 1.

FIG. 2 is a block diagram of the data processing unit of the data monitoring and detection system shown in FIG. 1 in accordance with certain embodiments. The data processing unit 102 thus may include one or more of an analog interface 201 configured to communicate with the sensor 101 (FIG. 1), a user input 202, and a temperature detection section 203, each of which is operatively coupled to a processor 204 such as a central processing unit (CPU). The data processing unit may include user input and/or interface components or may be free of user input and/or interface components.

Further shown in FIG. 2 are serial communication section 205 and an RF transmitter or transceiver 206, each of which is also operatively coupled to the processor 204. In one embodiment, the serial communication section 205 is in direct communication with the analog interface 201 via communication link 209, which may be configured for bi-directional communication. Moreover, a power supply 207, such as a battery, may also be provided in the data processing unit 102 to provide the necessary power for the data processing unit 102. Additionally, as can be seen from the Figure, clock 208 may be provided to, among others, supply real time information to the transmitter processor 204.

As can be seen in the embodiment of FIG. 2, the sensor unit 101 (FIG. 1) includes four contacts, three of which are electrodes—work electrode (W) 210, guard contact (G) 211, reference electrode (R) 212, and counter electrode (C) 213, each operatively coupled to the analog interface 201 of the data processing unit 102. In certain embodiments, each of the work electrode (W) 210, guard contact (G) 211, reference electrode (R) 212, and counter electrode (C) 213 may be made using a conductive material that may be applied by, e.g., chemical vapor deposition (CVD), physical vapor deposition, sputtering, reactive sputtering, printing, coating, ablating (e.g., laser ablation), painting, dip coating, etching, and the like. Materials include but are not limited to aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The processor 204 may be configured to generate and/or process control signals to the various sections of the data processing unit 102 during the operation of the data processing unit 102. In certain embodiments, the processor 204 also includes memory (not shown) for storing data such as the identification information for the data processing unit 102, as well as the data associated with signals received from the sensor 101. The stored information may be retrieved and processed for transmission to the primary receiver unit 104 under the control of the processor 204. Furthermore, the power supply 207 may include a commercially available battery.

In certain embodiments, a manufacturing process of the data processing unit 102 may place the data processing unit 102 in the lower power, non-operating state (i.e., post-manufacture sleep mode). In this manner, the shelf life of the data processing unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present disclosure, the power supply unit 207 is configured to provide the necessary power to each of the components of the data processing unit 102 shown in FIG. 2.

Referring back to FIG. 2, the power supply section 207 of the data processing unit 102 in one embodiment may include a rechargeable battery unit that may be recharged by a separate power supply recharging unit (for example, provided in the receiver unit 104) so that the data processing unit 102 may be powered for a longer period of usage time. In certain embodiments, the data processing unit 102 may be configured without a battery in the power supply section 207, in which case the data processing unit 102 may be configured to receive power from an external power supply source (for example, a battery, electrical outlet, etc.) as discussed in further detail below.

Referring yet again to FIG. 2, a temperature detection section 203 of the data processing unit 102 is configured to monitor the temperature of the skin near the sensor insertion site. The temperature reading may be used to adjust the analyte readings obtained from the analog interface 201. Also shown is a leak detection circuit 214 coupled to the guard trace (G) 211 and the processor 204 in the data processing unit 102 of the data monitoring and management system 100. The leak detection circuit 214 may be configured to detect leakage current in the sensor 101 to determine whether the measured sensor data are corrupt or whether the measured data from the sensor 101 is accurate. Such detection may trigger a notification to the user.

Figure 3:
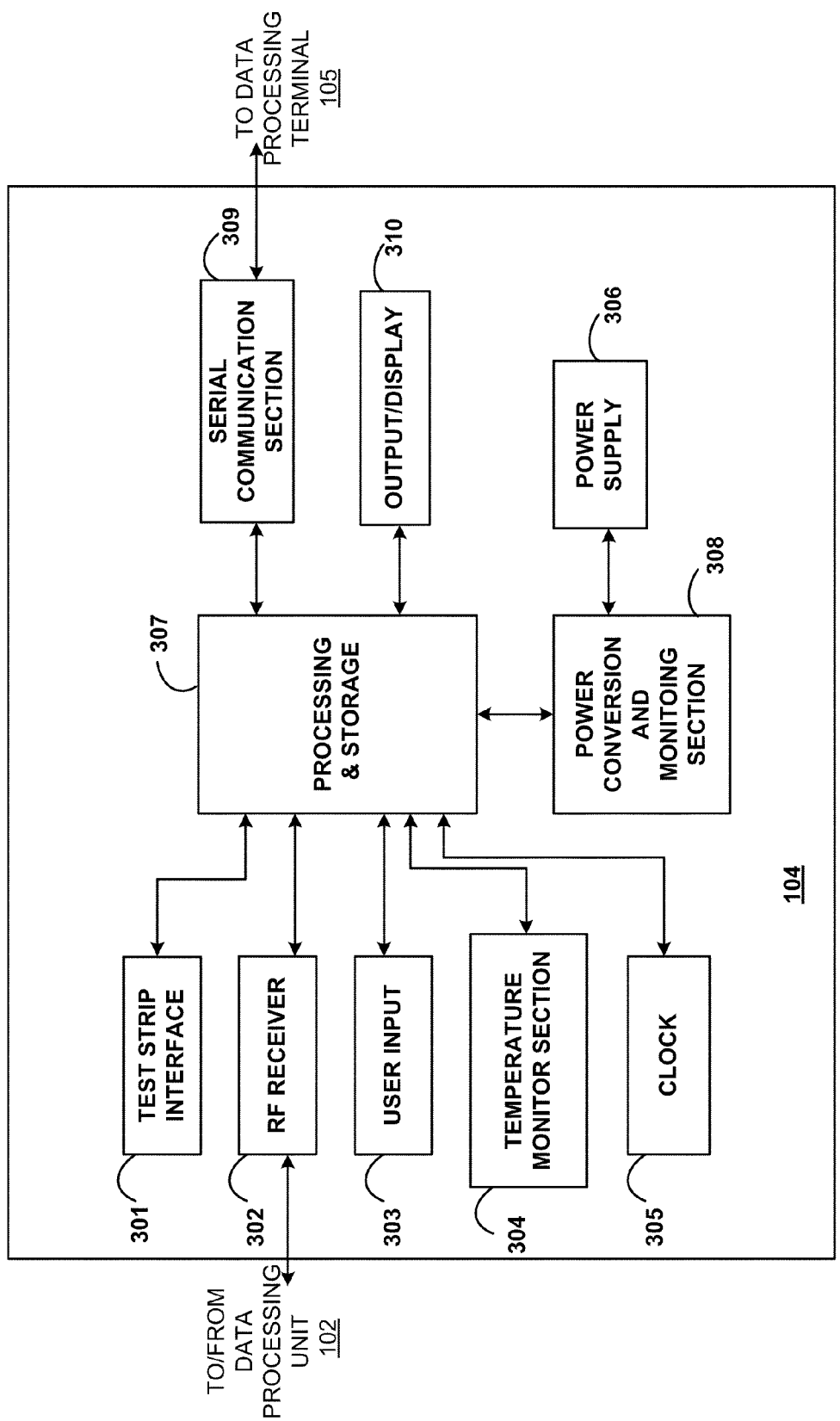
FIG. 3 shows a block diagram of an embodiment of a receiver/monitor unit of the data monitoring and management system of FIG. 1.

FIG. 3 is a block diagram of a receiver/monitor unit such as the primary receiver unit 104 of the data monitoring and management system shown in FIG. 1 in accordance with certain embodiments. The primary receiver unit 104 includes one or more of: a blood glucose test strip interface 301, an RF receiver 302, an input 303, a temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the processing and storage section 307. Moreover, also shown are a receiver serial communication section 309, and an output 310, each operatively coupled to the processing and storage unit 307. The receiver may include user input and/or interface components or may be free of user input and/or interface components.

In certain embodiments, the test strip interface 301 includes a glucose level testing portion to receive a blood (or other body fluid sample) glucose test or information related thereto. For example, the interface may include a test strip port to receive a glucose test strip. The device may determine the glucose level of the test strip, and optionally display (or otherwise notice) the glucose level on the output 310 of the primary receiver unit 104. Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. FreeStyle® blood glucose test strips from Abbott Diabetes Care Inc. Glucose information obtained by the in vitro glucose testing device may be used for a variety of purposes, computations, etc. For example, the information may be used to calibrate sensor 101, confirm results of the sensor 101 to increase the confidence thereof (e.g., in instances in which information obtained by sensor 101 is employed in therapy related decisions), etc.

In one aspect, the RF receiver 302 is configured to communicate, via the communication link 103 (FIG. 1) with the RF transmitter 206 of the data processing unit 102, to receive encoded data from the data processing unit 102 for, among others, signal mixing, demodulation, and other data processing. The input 303 of the primary receiver unit 104 is configured to allow the user to enter information into the primary receiver unit 104 as needed. In one aspect, the input 303 may include keys of a keypad, a touch-sensitive screen, and/or a voice-activated input command unit, and the like. The temperature monitor section 304 may be configured to provide temperature information of the primary receiver unit 104 to the processing and control section 307, while the clock 305 provides, among others, real time or clock information to the processing and storage section 307.

Each of the various components of the primary receiver unit 104 shown in FIG. 3 is powered by the power supply 306 (or other power supply) which, in certain embodiments, includes a battery. Furthermore, the power conversion and monitoring section 308 is configured to monitor the power usage by the various components in the primary receiver unit 104 for effective power management and may alert the user, for example, in the event of power usage which renders the primary receiver unit 104 in sub-optimal operating conditions. The serial communication section 309 in the primary receiver unit 104 is configured to provide a bi-directional communication path from the testing and/or manufacturing equipment for, among others, initialization, testing, and configuration of the primary receiver unit 104. Serial communication section 104 can also be used to upload data to a computer, such as time-stamped blood glucose data. The communication link with an external device (not shown) can be made, for example, by cable (such as USB or serial cable), infrared (IR) or RF link. The output/display 310 of the primary receiver unit 104 is configured to provide, among others, a graphical user interface (GUI), and may include a liquid crystal display (LCD) for displaying information. Additionally, the output/display 310 may also include an integrated speaker for outputting audible signals as well as to provide vibration output as commonly found in handheld electronic devices, such as mobile telephones, pagers, etc. In certain embodiments, the primary receiver unit 104 also includes an electro-luminescent lamp configured to provide backlighting to the output 310 for output visual display in dark ambient surroundings.

Referring back to FIG. 3, the primary receiver unit 104 may also include a storage section such as a programmable, non-volatile memory device as part of the processing and storage section 307, or provided separately in the primary receiver unit 104, operatively coupled to a processor. The processor may be configured to perform Manchester decoding (or other protocol(s)) as well as error detection and correction upon the encoded data received from the data processing unit 102 via the communication link 103.

In further embodiments, the data processing unit 102 and/or the primary receiver unit 104 and/or the secondary receiver unit 106, and/or the data processing terminal/infusion section 105 may be configured to receive the blood glucose value wirelessly over a communication link from, for example, a blood glucose meter. In further embodiments, a user manipulating or using the analyte monitoring system 100 (FIG. 1) may manually input the blood glucose value using, for example, a user interface (for example, a keyboard, keypad, voice commands, and the like) incorporated in the one or more of the data processing unit 102, the primary receiver unit 104, secondary receiver unit 105, or the data processing terminal/infusion section 105.

Additional detailed descriptions are provided in U.S. Pat. Nos. 5,262,035; 5,264,104; 5,262,305; 5,320,715; 5,593,852; 6,175,752; 6,650,471; 6,746,582, and in application Ser. No. 10/745,878 filed Dec. 26, 2003 entitled "Continuous Glucose Monitoring System and Methods of Use", each of which is incorporated herein by reference.

FIG. 4 schematically shows an embodiment of an analyte sensor in accordance with the present disclosure. The sensor 400 includes electrodes 401, 402 and 403 on a base 404. The sensor may be wholly implantable in a user or may be configured so that only a portion is positioned within (internal) a user and another portion outside (external) a user. For example, the sensor 400 may include a portion positionable above a surface of the skin 410, and a portion positioned below the skin. In such embodiments, the external portion may include contacts (connected to respective electrodes of the second portion by traces) to connect to another device also external to the user such as a transmitter unit. While the embodiment of FIG. 4 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc.

FIG. 5A shows a perspective view of an embodiment of an electrochemical analyte sensor 500 having a first portion (which in this embodiment may be characterized as a major portion) positionable above a surface of the skin 510, and a second portion (which in this embodiment may be characterized as a minor portion) that includes an insertion tip 530 positionable below the skin, e.g., penetrating through the skin and into, e.g., the subcutaneous space 520, in contact with the user's biofluid such as interstitial fluid. Contact portions of a working electrode 501, a reference electrode 502, and a counter electrode 503 are positioned on the portion of the sensor 500 situated above the skin surface 510. Working electrode 501, a reference electrode 502, and a counter electrode 503 are shown at the second section and particularly at the insertion tip 530. Traces may be provided from the electrode at the tip to the contact, as shown in FIG. 5A. It is to be understood that greater or fewer electrodes may be provided on a sensor. For example, a sensor may include more than one working electrode and/or the counter and reference electrodes may be a single counter/reference electrode, etc.

FIG. 5B shows a cross sectional view of a portion of the sensor 500 of FIG. 5A. The electrodes 501, 502 and 503, of the sensor 500 as well as the substrate and the dielectric layers are provided in a layered configuration or construction. For example, as shown in FIG. 5B, in one aspect, the sensor 500 (such as the sensor unit 101 FIG. 1), includes a substrate layer 504, and a first conducting layer 501 such as carbon, gold, etc., disposed on at least a portion of the substrate layer 504, and which may provide the working electrode. Also shown disposed on at least a portion of the first conducting layer 501 is a sensing layer 508.

Referring back to FIG. 5B, a first insulation layer such as a first dielectric layer 505 is disposed or layered on at least a portion of the first conducting layer 501, and further, a second conducting layer 509 may be disposed or stacked on top of at least a portion of the first insulation layer (or dielectric layer) 505. As shown in FIG. 5B, the second conducting layer 509 may provide the reference electrode 502, and in one aspect, may include a layer of silver/silver chloride (Ag/AgCl), gold, etc.

Referring still again to FIG. 5B, a second insulation layer 506 such as a dielectric layer in one embodiment may be disposed or layered on at least a portion of the second conducting layer 509. Further, a third conducting layer 503 may provide the counter electrode 503. It may be disposed on at least a portion of the second insulation layer 506. Finally, a third insulation layer 507 may be disposed or layered on at least a portion of the third conducting layer 503. In this manner, the sensor 500 may be layered such that at least a portion of each of the conducting layers is separated by a respective insulation layer (for example, a dielectric layer).

The embodiment of FIGS. 5A and 5B show the layers having different lengths. Some or all of the layers may have the same or different lengths and/or widths.

In certain embodiments, some or all of the electrodes 501, 502, 503 may be provided on the same side of the substrate 504 in the layered construction as described above, or alternatively, may be provided in a co-planar manner such that two or more electrodes may be positioned on the same plane (e.g., side-by side (e.g., parallel) or angled relative to each other) on the substrate 504. For example, co-planar electrodes may include a suitable spacing there between and/or include dielectric material or insulation material disposed between the conducting layers/electrodes. Furthermore, in certain embodiments one or more of the electrodes 501, 502, 503 may be disposed on opposing sides of the substrate 504. In such embodiments, contact pads may be on the same or different sides of the substrate. For example, an electrode may be on a first side and its respective contact may be on a second side, e.g., a trace connecting the electrode and the contact may traverse through the substrate.

In certain embodiments, the data processing unit 102 may be configured to perform sensor insertion detection and data quality analysis, information pertaining to which may also transmitted to the primary receiver unit 104 periodically at the predetermined time interval. In turn, the receiver unit 104 may be configured to perform, for example, skin temperature compensation/correction as well as calibration of the sensor data received from the data processing unit 102.

As noted above, analyte sensors may include an analyte-responsive enzyme in a sensing layer. Some analytes, such as oxygen, can be directly electrooxidized or electroreduced on a sensor, and more specifically at least on a working electrode of a sensor. Other analytes, such as glucose and lactate, require the presence of at least one electron transfer agent and/or at least one catalyst to facilitate the electrooxidation or electroreduction of the analyte. Catalysts may also be used for those analyte, such as oxygen, that can be directly electrooxidized or electroreduced on the working electrode. For these analytes, each working electrode includes a sensing layer (see for example sensing layer 508 of FIG. 5B) formed proximate to or on a surface of a working electrode. In many embodiments, a sensing layer is formed near or on only a small portion of at least a working electrode.

A variety of different sensing layer configurations may be used. In certain embodiments, the sensing layer is deposited on the conductive material of a working electrode. The sensing layer may extend beyond the conductive material of the working electrode. In some cases, the sensing layer may also extend over other electrodes, e.g., over the counter electrode and/or reference electrode (or counter/reference is provided). The sensing layer may be integral with the material of an electrode.

A sensing layer that is in direct contact with the working electrode may contain an electron transfer agent to transfer electrons directly or indirectly between the analyte and the working electrode, and/or a catalyst to facilitate a reaction of the analyte. For example, a glucose, lactate, or oxygen electrode may be formed having a sensing layer which contains a catalyst, such as glucose oxidase, lactate oxidase, or laccase, respectively, and an electron transfer agent that facilitates the electrooxidation of the glucose, lactate, or oxygen, respectively.

In certain embodiments which include more than one working electrode, one or more of the working electrodes do not have a corresponding sensing layer, or have a sensing layer which does not contain one or more components (e.g., an electron transfer agent and/or catalyst) needed to electrolyze the analyte. Thus, the signal at this working electrode corresponds to background signal which may be removed from the analyte signal obtained from one or more other working electrodes that are associated with fully-functional sensing layers by, for example, subtracting the signal.

In certain embodiments, the sensing layer includes one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes such as ferrocene. Examples of inorganic redox species are hexacyanoferrate (III), ruthenium hexamine etc.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic, or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

One type of polymeric electron transfer agent contains a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, such as 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone (PQQ) dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent (which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

Certain embodiments include a Wired Enzyme™ sensing layer that works at a gentle oxidizing potential, e.g., a potential of about +40 mV. This sensing layer uses an osmium (Os)-based mediator designed for low potential operation and is stably anchored in a polymeric layer. Accordingly, in certain embodiments the sensing element is redox active component that includes (1) Osmium-based mediator molecules attached by stable (bidente) ligands anchored to a polymeric backbone, and (2) glucose oxidase enzyme molecules. These two constituents are crosslinked together.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may serve many functions, e.g., functionalities of a biocompatible layer and/or interferent-eliminating layer may be provided by the mass transport limiting layer.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

According certain embodiments, a membrane is formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over an enzyme-containing sensing layer and allowing the solution to cure for about one to two days or other appropriate time period. The crosslinker-polymer solution may be applied to the sensing layer by placing a droplet or droplets of the solution on the sensor, by dipping the sensor into the solution, or the like. Generally, the thickness of the membrane is controlled by the concentration of the solution, by the number of droplets of the solution applied, by the number of times the sensor is dipped in the solution, or by any combination of these factors. A membrane applied in this manner may have any combination of the following functions: (1) mass transport limitation, i.e., reduction of the flux of analyte that can reach the sensing layer, (2) biocompatibility enhancement, or (3) interferent reduction.

The electrochemical sensors may employ any suitable measurement technique. For example, may detect current or may employ potentiometry. Technique may include, but are not limited to amperometry, coulometry, voltammetry. In some embodiments, sensing systems may be optical, calorimetric, and the like.

In certain embodiments, the sensing system detects hydrogen peroxide to infer glucose levels. For example, a hydrogen peroxide-detecting sensor may be constructed in which a sensing layer includes enzyme such as glucose oxides, glucose dehydrogensae, or the like, and is positioned proximate to the working electrode. The sending layer may be covered by a membrane that is selectively permeable to glucose. Once the glucose passes through the membrane, it is oxidized by the enzyme and reduced glucose oxidase can then be oxidized by reacting with molecular oxygen to produce hydrogen peroxide.

Certain embodiments include a hydrogen peroxide-detecting sensor constructed from a sensing layer prepared by crosslinking two components together, for example: (1) a redox compound such as a redox polymer containing pendent Os polypyridyl complexes with oxidation potentials of about +200 mV vs. SCE, and (2) periodate oxidized horseradish peroxidase (HRP). Such a sensor functions in a reductive mode; the working electrode is controlled at a potential negative to that of the Os complex, resulting in mediated reduction of hydrogen peroxide through the HRP catalyst.

In another example, a potentiometric sensor can be constructed as follows. A glucose-sensing layer is constructed by crosslinking together (1) a redox polymer containing pendent Os polypyridyl complexes with oxidation potentials from about −200 mV to +200 mV vs. SCE, and (2) glucose oxidase. This sensor can then be used in a potentiometric mode, by exposing the sensor to a glucose containing solution, under conditions of zero current flow, and allowing the ratio of reduced/oxidized Os to reach an equilibrium value. The reduced/oxidized Os ratio varies in a reproducible way with the glucose concentration, and will cause the electrode's potential to vary in a similar way.

A sensor may also include an active agent such as an anticlotting and/or antiglycolytic agent(s) disposed on at least a portion a sensor that is positioned in a user. An anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents. Embodiments may include an antiglycolytic agent or precursor thereof. Examples of antiglycolytic agents are glyceraldehyde, fluoride ion, and mannose. The term "antiglycolytic" is used broadly herein to include any substance that at least retards glucose consumption of living cells.

Sensors described herein may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors, such as but not limited to glucose concentration and/or temperature and/or rate of change of glucose, etc.

Calibration may be accomplished using an in vitro test strip or other calibrator, e.g., a small sample test strip such as a test strip that requires less than about 1 microliter of sample (for example FreeStyle® blood glucose monitoring test strips from Abbott Diabetes Care Inc. of Alameda, Calif.). For example, test strips that require less than about 1 nanoliter of sample may be used. In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is obtained firstly. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate. In certain embodiments, a system need only be calibrated once by a user, where recalibration of the system is not required.

An analyte system may include an optional alarm system that, e.g., based on information from a processor, warns the patient of a potentially detrimental condition of the analyte. For example, if glucose is the analyte, an alarm system may warn a user of conditions such as hypoglycemia and/or hyperglycemia and/or impending hypoglycemia, and/or impending hyperglycemia. An alarm system may be triggered when analyte levels reach or exceed a threshold value. An alarm system may also, or alternatively, be activated when the rate of change or acceleration of the rate of change in analyte level increase or decrease approaches, reaches or exceeds a threshold rate or acceleration. For example, in the case of a glucose monitoring system, an alarm system may be activated if the rate of change in glucose concentration exceeds a threshold value which might indicate that a hyperglycemic or hypoglycemic condition is likely to occur. A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

The subject invention also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. The sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Figure 6:
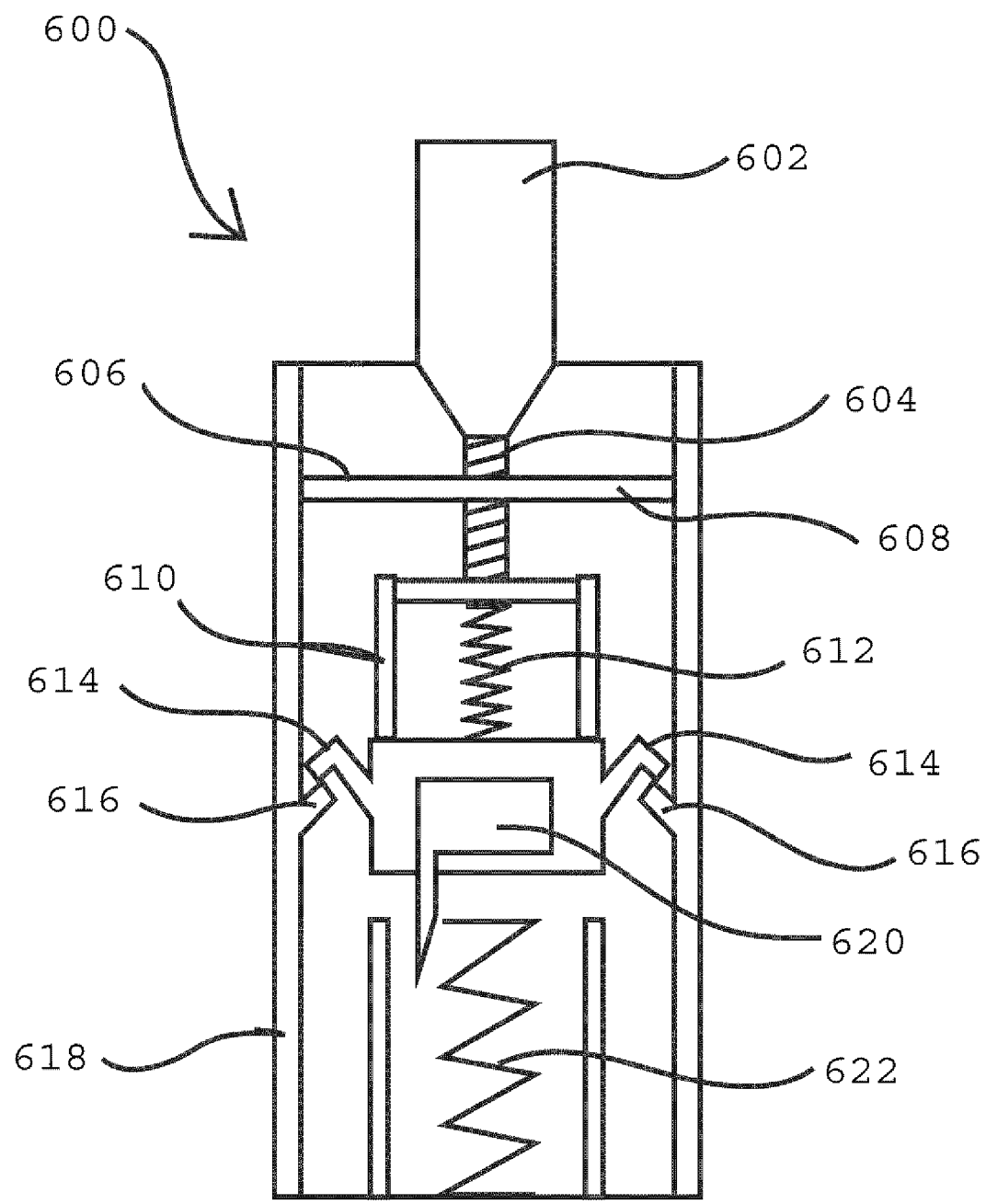
FIG. 6 illustrates an example of a sensor insertion unit, or sensor delivery unit, used in one or more embodiments of the present disclosure.

FIG. 6 illustrates an example of a sensor insertion unit, or sensor delivery unit, used in one or more embodiments of the present disclosure. Referring to FIG. 6, an inserter 600 embodiment having a micrometer style head or knob 602 is shown. Knob 602 may be attached to a threaded rod 604. Threaded rod 604 may be received through a threaded hole or insert in fixed housing cross member 606. A distal end of threaded rod 604 may be rotatably or fixedly attached to compression member 608. Compression member 608 may be movable with respect to carrier 610 for compressing drive spring 612 therebetween.

Carrier 610 may be provided with barbed fingers 614 for engaging stops 616 within housing 618 to releasably retain carrier 610 in a cocked position, similar to the arrangements of embodiments described above. Inserter 600 may be provided with an actuator button for releasing barbed fingers 614 from stops 616 as also previously described, allowing drive spring 612 to drive carrier 610 downward with introducer sharp and/or sensor 620 to be inserted into the patient's skin. A return spring 622 may also be provided to retract carrier 610 into housing 618 after sensor insertion.

In another embodiment of the present disclosure, other types of sensor delivery units may be used in place of the sensor delivery unit shown in FIG. 6 and described above.

In one aspect, the sensor delivery unit or inserter 600 (FIG. 6) may be assembled and packaged with the analyte sensor 620 prior to exposing the assembly to a sterilization process such that the entire sensor insertion assembly including the analyte sensor 620 is exposed to one or more sterilization processes using, for example electron beam irradiation. It is to be noted that while electron beam irradiation for sterilization is discussed herein, in accordance with other aspects of the present disclosure, different or additional sterilization may be provided to all or one or more component, or part of the assembly including the sensor delivery unit or inserter 600 (FIG. 6) and with the analyte sensor 620.

Electron beam irradiation may be used for the sterilization of a medical device. The process of using electron beam irradiation inactivates or kills microorganisms or other contaminants on or within the medical device such as the sensor insertion assembly. In one aspect, an electron beam irradiation sterilization process may include sweeping an intense beam of high-energy electrons across the target device. Electron beam irradiation may be a penetrating process, allowing the target medical device to be already packaged in its final packaging before the irradiation process.

Thus, by sterilizing the medical device such as the assembled insertion device assembly including the analyte sensor after it has been packaged, the possibility of contamination during the time between sterilization and packaging is reduced. Furthermore, electron beam irradiation may penetrate most commonly used packaging materials, including, but not limited to, most plastic, metal, and cardboard packaging materials such that sterilizing packaged medical device assembly such as the sensor insertion device and the sensor provided within a packaging material yield effective sterilization of the insertion device and the sensor assembly without the packaging material diminishing the effects of the sterilization process.

Figure 7A:
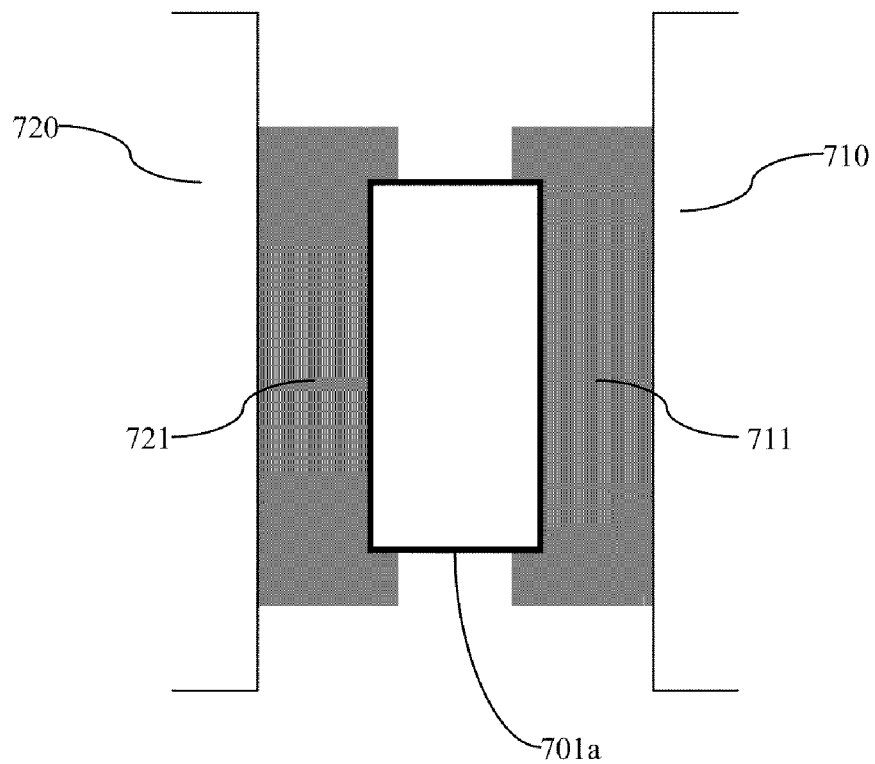
FIGS. 7A and 7B are representations of two methods of electron beam irradiation sterilization.
Figure 7B:
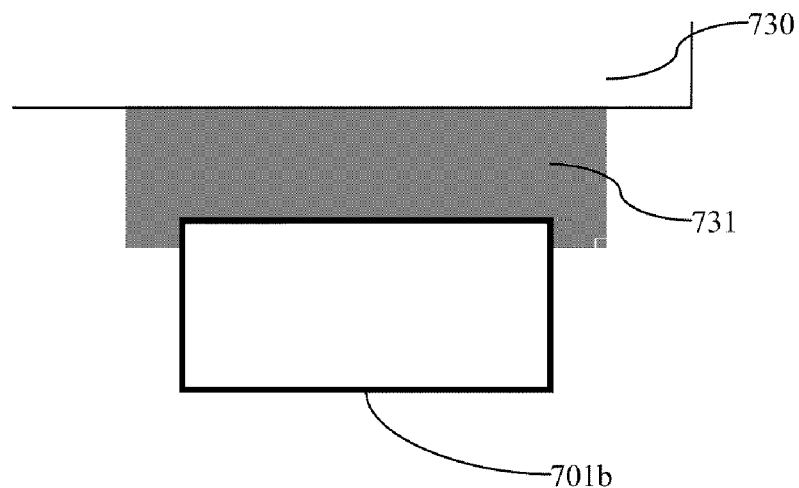

Referring now to the Figures, in one aspect, FIGS. 7A and 7B show two approaches for electron beam irradiation sterilization in aspects of the present disclosure. For example, electron beam irradiation sterilization may be performed with two electron beam accelerators, such as shown in FIG. 7A, or with a single electron beam accelerator as shown in FIG. 7B. More than two electron beam accelerators may be used if, e.g., a target, such as a packaging, device, or material, is large or dense enough such that more than two sides of electron beams are desired for sterilization.

In one aspect, electron beam accelerators may be used to accelerate electrons into the concentrated highly charged electron stream used for the electron beam irradiation. As materials pass through the stream of electrons, energy from the stream may be absorbed. The absorption of this energy alters chemical and biological bonds. At certain levels of absorption, also known as the absorption dose, DNA chains and reproductive cells of microorganisms may be destroyed, therefore effectively sterilizing the target assembly or package. The irradiation dosage is important, as too low of a dosage may not result in complete sterilization, while too high of a dosage may result in adverse effects on the materials of the target, packaging, or the device being sterilized.

Depending on target size, material, density, and desired irradiation level, sterilization by use of electron beam irradiation may be performed in as little as one minute per package. As degradation of materials of the target assembly in either the packaging or the device itself may correlate to the irradiation time, the less time required to irradiate the target packaging or device to the target irradiation dosage, the less degradation of materials may occur. Furthermore, the sterilized target may not require any aeration time after sterilization before being ready for transport and/or distribution.

In one aspect, the electron beam irradiation process may penetrate inside packaging of devices to be sterilized, therefore allowing sterilization after devices are packaged in their final packaging configuration. This decreases the risk of contamination between the sterilization process and the final packaging process. The penetration power of the electron beam irradiation correlates to the package size, package orientation, package density, and electron beam accelerator power. The larger and denser the packaging, the more powerful of an electron beam may be required to achieve full penetration.

Referring back to FIG. 7A, two electron beam accelerators 710, 720 may be used to achieve complete sterilization. One electron beam accelerator 710 may be positioned on one side of the target 701*a*, while the second electron beam accelerator 720 may be positioned on the opposite side. This configuration may allow for the two electron beams 711, 721 to share the penetration requirements in order to irradiate the interior of the target 701*a* to the desired irradiation dosage.

Referring now to FIG. 7B, a single electron beam accelerator 730 may be used for electron beam irradiation sterilization. In this case, a single electron beam accelerator 730 may produce electron beam 731 to irradiate a package 701*b*. This approach may be more effective for sterilizing packages that may be smaller or less dense, thus not necessitating the use of two or more electron beams to achieve full penetration for sterilization.

Other embodiments may include, but are not limited to, the use of a single electron beam accelerator to irradiate a single side of a target, followed by a process of rotating the target and further irradiating a second side with the same electron beam accelerator. This may result in having a similar effect to the method of using two electron beam accelerators, however, would only require the hardware of a single electron beam accelerator. Furthermore, three or more electron beam accelerators may be used for penetration from more than two sides of a target, such as, for example, from the left, right, and top sides.

The determination of how many electron beam accelerators to use in the electron beam irradiation sterilization of a target may be determined based upon size and density of a target in combination with the power of the electron beam accelerators that is used in the process and the internal and surface irradiation dosage minimums and maximums desired for full sterilization without compromising the integrity of the target, packaging, or the device to be sterilized.

Furthermore, the electron beam irradiation process may include a continuous exposure or an intermittent exposure, and the electron beam accelerator may be of a continuous or a varying power, depending upon available machinery and determinations to achieve the desired internal and surface dosage limitations.

Figure 8A:
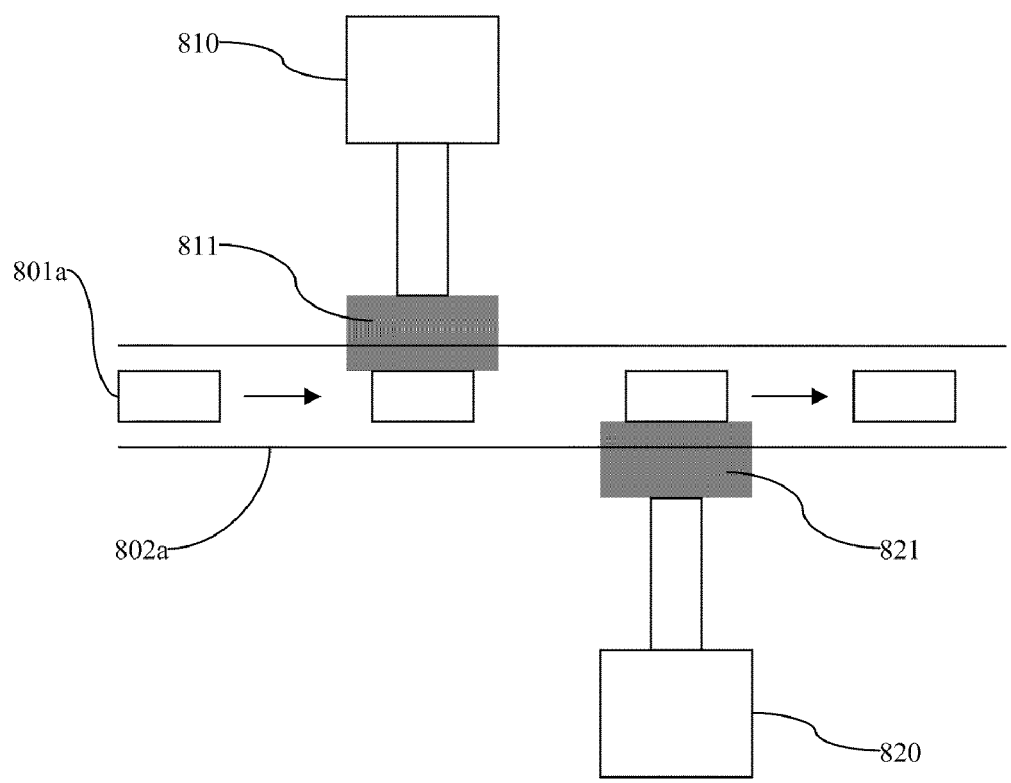
FIGS. 8A and 8B are representations of two systems for electron beam irradiation sterilization.
Figure 8B:
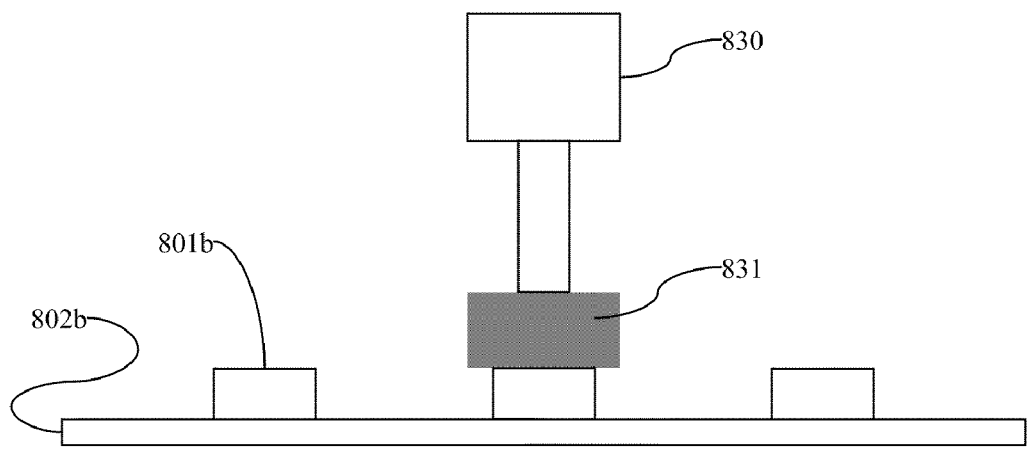

FIGS. 8A and 8B illustrate systems for electron beam irradiation sterilization in accordance with aspects of the present disclosure. Referring to FIG. 8A, a system for electron beam irradiation sterilization using two electron beam accelerators 810, 820 is shown. A target, such as a packaging containing a device (such as the packaging assembly including the sensor delivery unit and the analyte sensor) intended for sterilization 801*a* may be placed on a conveyor belt 802*a*, or equivalent, for passing by the electron beams 811, 821 generated by the electron beam accelerators 810, 820.

Referring to FIG. 8A, a first electron beam accelerator 810 may be placed on one side of the conveyor 802*a*, allowing for the electron beam 811 to irradiate the target 801*a* from a first side. This first irradiation may not be required to have full penetration, as the second electron beam 821 may irradiate from the opposite side, thus completing the penetration of the electron beams. After passing by the first electron beam 811 for a predetermined period of time at a preset power level, the target 801*a* may pass by the second electron beam 821, also for another predetermined period of time at a preset power. The amount of the predetermined time and preset power of each electron beam 811, 821 may be determined based on the size and density of the target 801*a* and the desired surface and internal electron beam irradiation dosages.

Referring to FIG. 8B, a system for electron beam irradiation sterilization using a single electron beam accelerator 830 is shown. A target, such as a packaging including sensor insertion device and the analyte sensor, intended for sterilization 801*b* may be placed on a conveyor belt 802*b*, or equivalent, for passing by an electron beam 831 generated by an electron beam accelerator 830. The electron beam accelerator 830 may be placed on one side or above (as shown in FIG. 8B) of the conveyor 802*b*, allowing for the electron beam 831 to irradiate the target 801*b* for a predetermined period of time at a preset power level. The amount of the predetermined time and preset power level of the electron beam 831 may be determined based on the size and density of the target 801*b* and the desired surface and internal electron beam irradiation dosages.

Other embodiments may include, but are not limited to, systems using three or more electron beam accelerators or systems using a single electron beam accelerator with rotational functions to irradiate a package from multiple sides using the same electron beam.

In one embodiment of the present disclosure, electron beam irradiation may be used for the sterilization of an analyte sensor. Furthermore, electron beam irradiation may be used for the sterilization of an analyte sensor and an analyte sensor insertion kit or an analyte sensor delivery unit.

In another embodiment of the present disclosure, electron beam irradiation may be used for the sterilization of an analyte sensor, analyte sensor delivery unit, or a continuous monitoring analyte system.

Figure 9:
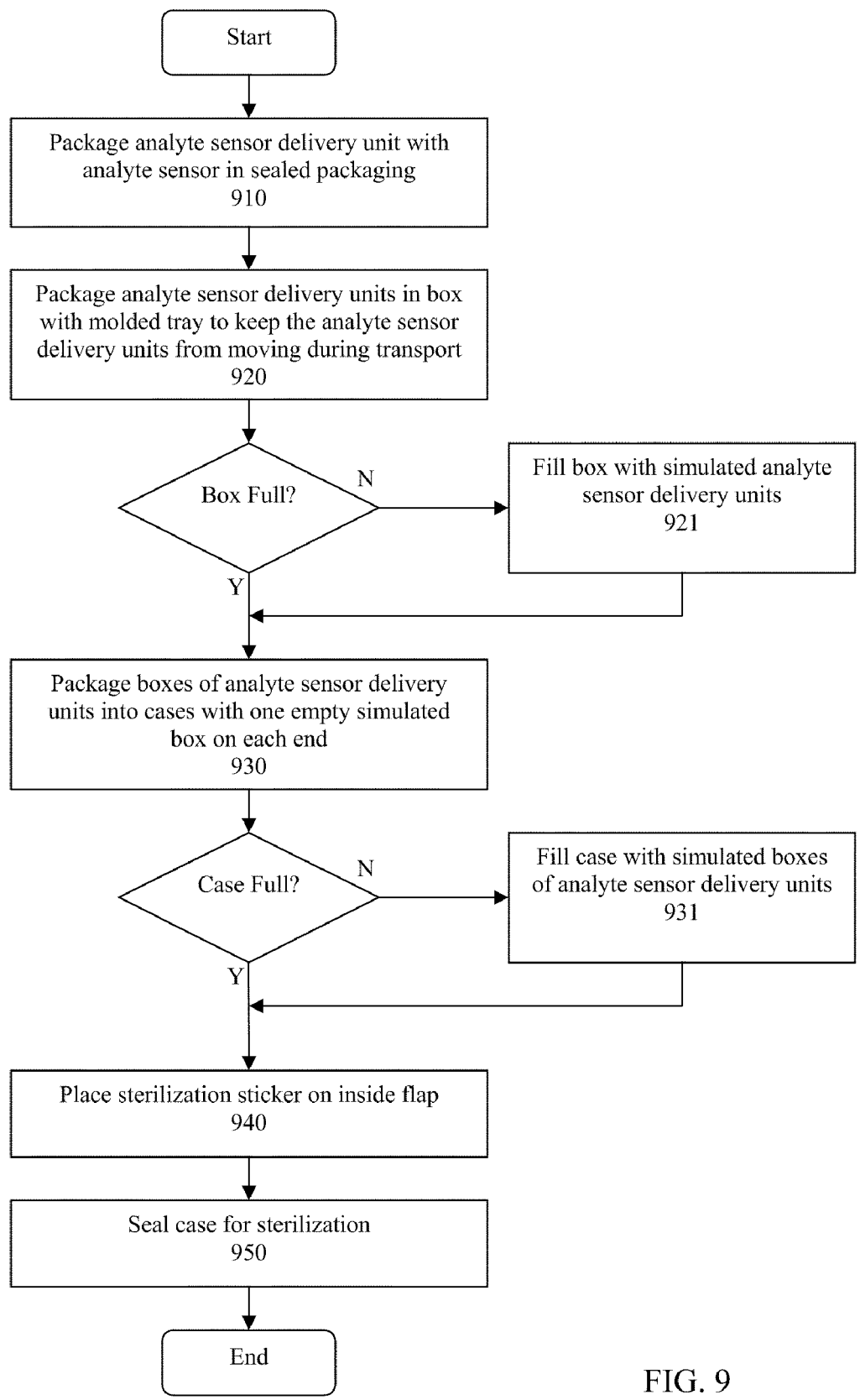
FIG. 9 is a flow chart illustrating analyte sensor delivery unit packaging for transport to a facility for electron beam irradiation sterilization.

FIG. 9 is a flow chart representing steps that may be used for packaging analyte sensor delivery units for transport to a facility for electron beam irradiation sterilization. Referring to FIG. 9, an analyte sensor delivery unit, including an analyte sensor, may be packaged in an individual airtight sealed packaging 910. The packaging may be sufficiently small for ease of transport and shelving, and also sufficiently sturdy to help prevent damage to the analyte sensor and analyte sensor delivery unit.

A predetermined number of the packaged analyte sensor delivery units may be packaged into a box, for example, constructed of a cardboard material, for handling 920. The box may alternatively be constructed from materials including, but not limited to, plastics, woods, or metals. The cardboard box may be designed in such a manner as to allow for the packaged analyte sensor delivery units to remain stationary during transport, by use of, for example, slots or a molded tray. It is desirable that the analyte sensor delivery units remain stationary during transport so as to minimize the chance or possibility of the analyte sensor delivery units incurring damages during transport. In the case that the cardboard box is not filled to capacity with analyte sensor delivery units, properly labeled simulated or dummy units may be placed in the empty spots in the cardboard box 921.

Boxes of analyte sensor delivery units that include simulated units mixed with actual device assemblies may be labeled accordingly to respectively identify each other. The cardboard boxes of analyte sensor delivery units may be then packaged into larger cases, preferably constructed of a cardboard material, for further ease of handling 930. The case may alternatively be constructed from materials including, but not limited to, plastics, woods, or metals. The boxes of analyte sensor delivery units may be oriented in the same direction within the cardboard case for even irradiation in the sterilization process.

In order to protect the analyte sensor delivery units during sterilization and/or to attain the desired sterilization level, boxes or containers filled with simulated units may be placed at each end of the case. In the case that the case is not filled to capacity with boxes of assembled analyte sensor delivery units including analyte sensors, extra boxes filled with simulated units may be placed in the case 931. Boxes filled completely with simulated units and boxes filled partially with simulated units may be placed at the two ends of the cases, while boxes filled completely with analyte sensors delivery units may be placed in the center of the case.

A sterilization sticker may be placed on the side flap of the case 940 to indicate completion of the sterilization process, and the case may be sealed for transport to the facility for electron beam irradiation sterilization 950. Cases containing partially filled boxes or more than the two required simulated boxes, may be labeled as partial cases.

In another embodiment, the analyte sensors alone, without the analyte sensor delivery unit, may be packaged in airtight packaging before sterilized using electron beam irradiation, or the analyte sensor and the analyte delivery unit may be separately packaged and separately electron beam sterilized.

Figure 10:
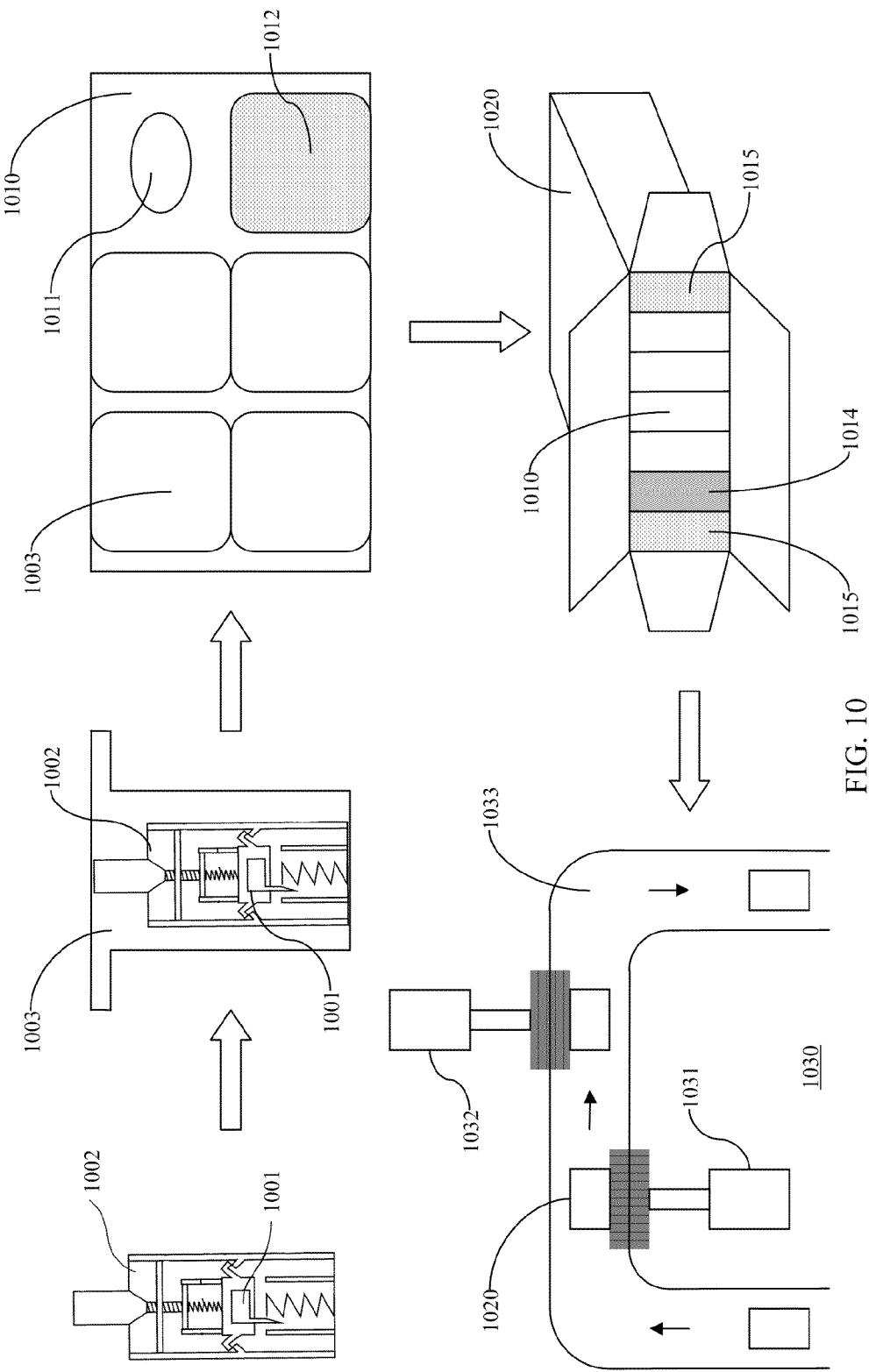
FIG. 10 is a flow diagram illustrating a system for sterilizing an analyte sensor and analyte sensor delivery unit.

FIG. 10 illustrates a system for sterilizing an analyte sensor and analyte sensor delivery unit in one aspect. Referring to FIG. 10, in one embodiment of the present disclosure, an analyte sensor 1001 may be loaded into an analyte sensor delivery unit 1002. This analyte sensor 1001 and analyte sensor delivery unit 1002 may be a part of a continuous analyte monitoring system. The analyte sensor delivery unit 1002 assembled with the analyte sensor 1001 may be packaged in an air tight packaging 1003. A predetermined number of packages 1003 may be placed into a box 1010, which may have slots 1011 to ensure the stability of the packages 1003 when placed inside the box 1010. The stability of the packages 1003 avoids potential damage to the analyte sensor delivery unit 1002 and the sensor 1001 during transport.

Additionally, in the case where there are insufficient number of packages 1003 to fill the box 1010 completely, simulated or dummy packages 1012 may be used to fill the empty slots 1011. These simulated packages 1012 may be used to ensure uniformity throughout the package, and further, in determining the desired irradiation dosages/levels. Once filled, the boxes 1010 may be loaded into cases 1020. The cases 1020 may be designed to hold a specific number of boxes 1010, with two simulated boxes 1015, one on each end of the case 1020. The boxes 1010 may be loaded in the same orientation respective to one another to ensure consistency in the irradiation process.

In the case where there is insufficient number of boxes 1010 to fill the case 1020, additional simulated boxes 1015 may be used. Simulated boxes 1015 and partially filled boxes 1014 may be placed at the ends of the cases 1020. Once a case 1020 is loaded, it may be transported to the electron beam irradiation system 1030. The cases 1020 may be loaded onto a conveyer 1033, or equivalent, where they are exposed to the electron beams of one or more electron beam accelerators 1031, 1032. While FIG. 10 depicts a system 1030 including two electron beam accelerators 1031, 1032, within the scope of the present disclosure, the system may be designed to work with only one electron beam accelerator or three or more electron beam accelerators.

Referring back to FIG. 10, the cases 1020 may be irradiated from a first side by a first electron beam accelerator 1031 for a predetermined time period at a preset power level, in either a continuous irradiation or intermittent bursts. Thereafter, the cases 1020 may be irradiated from a second side by a second electron beam accelerator 1032 for a predetermined time period at a preset power level. These irradiation time periods and preset power levels may be ascertained based upon the desired internal and surface dosages desired. In one aspect, the sterilization of the packaged sensor delivery unit including the analyte sensor may include two sided irradiation using two electron beam accelerators, each with 6 MeV at 1 KW. This process may be configured to sterilize material size up to 24 inches long and 20 inches high with 12 inches in thickness, resulting in density multiplied by thickness equaling 4.5 g/cm$^2$ facing the electron beam.

In one aspect, the analyte sensor and the analyte sensor delivery unit in a sealed package may be electron beam irradiated to attain sterilization to at least approximately 25 kGy dose to produce approximately $10^{-6}$ SAL (sterility assurance level), or preferably at approximately 30 kGy target surface dose, and in one aspect, the dose for the electron beam irradiation may be between approximately 25 kGy and 60 kGy.

In another embodiment, electron beam irradiation may be used for the sterilization of part or the entirety of a continuous analyte monitoring system.

In another embodiment, electron beam irradiation may be used for the sterilization of part or the entirety of any medical device or medical device system.

In certain embodiments, of the present disclosure, medical device assembly for sterilization may include oen or more electronic components, an analyte sensor including active sensing agents and/or chemistry and/or biologics related to analyte sensing disposed on the sensor, a sensor delivery unit including a mounting unit, an insertion needle such as a sharp introducer and/or adhesive, or one or more combinations thereof. Exemplary configurations of such medical device assembly for sterilization may be found in for example, U.S. Pat. No. 6,175,752, and in U.S. Provisional Application No. 61/149,639 filed Feb. 3, 2009, entitled "Compact On-Body Physiological Monitoring Device and Methods Thereof", the disclosure of each of which are incorporated herein by reference in its entirety.

In particular, in embodiments of the present disclosure, sterilization procedures are provided that achieve sterilization to at a safe sterility assurance level, such as for example a $10^{-6}$ SAL, where the sterilization procedures are performed on the medical device assembly in post manufacturing condition, in fully or partically assembled state. In other embodiments, a lower or higher target SAL may be implemented depending upon the device or assembly for sterlization.

Some medical device assembly such as, for example analyte monitoring assembly, may include a plurality of components such as electronic components, such as a transmitter, microprocessor, memory device, and the like, a sensor including active sensing agents, such as enzymes related to analyte sensing, disposed on the sensor, a sensor delivery unit including, for example, an insertion needle, a mounting unit, such as an adhesive, or one or more combinations thereof. Each component may have varying limitations and/or requirements for sterilization, where certain sterilization routine may be ineffective or potentially damage the component of part of the overall assembly.

For example, e-beam irradiation based sterilization may damage the electronic components of the medical device assembly. Also, sterilization procedures that use high temperatures and/or high levels of humidity may cause damage to or erosion of the enzymes or other chemistry or biologics on analyte sensor that include enzymes, or other chemistry or biologics. Additionally, exposure to high levels of humidity used in conjunction with the sterilization routine may render the adhesive ineffective (or lessen the effectiveness or lifespan of the adhesive) when the assembly to be sterilized includes adhesive such as, for example, the mounting unit/base of the medical device assembly discussed above.

Accordingly, in aspects of the present disclosure, gaseous chemical sterilization, using, for example, ethylene oxide (EO), vaporized hydrogen peroxide (VHP), or nitrogen oxides, such as nitrogen dioxide ($NO_2$), at one or more controlled temperatures, humidity levels, and chemical concentrations are provided. In one aspect, the gaseous chemical sterilization routines described herein are configured to minimize or avoid damage to components, such as electronic components and chemical/biological components, while achieving a desired safe sterility assurance level (SAL), such as a $10^{-6}$ SAL or other acceptable or desirable level of SAL.

Figure 11:
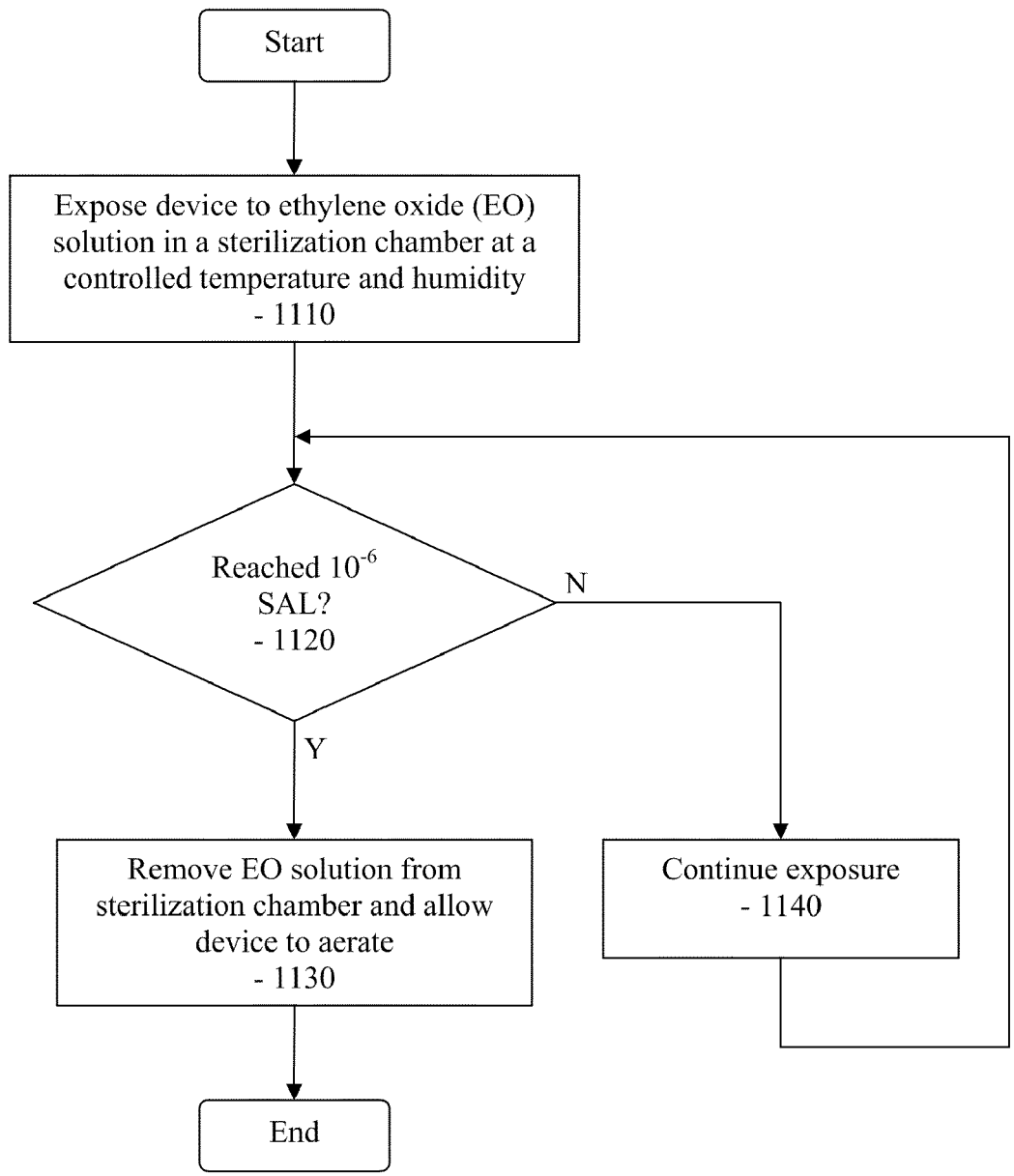
FIG. 11 is a flow chart illustrating an ethylene oxide based sterilization process in one aspect of the present disclosure.

FIG. 11 is a flow chart illustrating an ethylene oxide (EO) based sterilization process in one aspect of the present disclosure. Ethylene oxide sterilization, as well as other chemical sterilization methods, may potentially damage enzymes, chemistry or biologics unless the parameters including temperature, humidity, EO concentration, and EO exposure time are controlled or selected carefully. In one aspect, a custom cycle of EO sterilization may be used.

Referring to FIG. 11, in one embodiment, an ethylene oxide based sterilization procedure begins with providing the device, such as a medical device assembly, in a sterilization chamber at a controlled temperature and humidity (1110). The sterilization chamber may be used to contain the gaseous solution, to maintain a constant, controlled temperature and humidity, to keep the assembly free from outside contaminants during the sterilization process, and to protect any technicians involved in the sterilization process from exposure to potentially harmful chemicals. In one embodiment, the air in the sterilization chamber may be vacuumed out in order to more accurately control the temperature, humidity, pressure, and gas concentration within the sterilization chamber.

In some aspects, the EO based sterilization routine may use a temperature of up to approximately 60° C., a humidity level that is greater than 60%, such as 80% or greater, an EO concentration between approximately 200 mg/L and approximately 1000 mg/L, such as between approximately 400 mg/L and approximately 800 mg/L, such as approximately 600 mg/L, and an EO exposure time of between one and seven hours, such as an exposure time of between about three and five hours. With ethylene oxide sterilization, similar to other chemical sterilization techniques, the higher the temperature of the device or assembly within the sterilization chamber, the higher the level of lethality to contaminants, such as bacteria and spores. Additionally, higher levels of humidity also facilitate the absorption and desorption of EO into and out of the device for sterilization.

However, the high temperature and/or humidity level may be incompatible with and/or potentially cause damage (or render ineffective) to enzymes or other biological components provided on the component of the device or assembly for sterilization. To this end, in one aspect, the EO based sterilization routine may be implemented based on a lower temperature, for example a temperature lower than approximately 56° C., such as a temperature lower than approximately 50° C., such as approximately 45° C., and a lower humidity level, for example a humidity of less than approximately 50%, such as a humidity level of approximately 35%.

Referring still to FIG. 11, in one aspect, in the case where the EO based sterilization routine is implemented using a lower temperature and/or a lower humidity level, the EO exposure time may need to be increased (1140) to achieve a desired sterility assurance level, such as a $10^{-6}$ SAL (1120). In one embodiment, the exposure time may be calculated based upon an evaluation and determination of the exposure time value (D-value) determined based on the exposure time at a predetermined EO concentration that results in the destruction of 90% of the contaminant organism's population. In other embodiments, the exposure time may be based upon user experience, testing, trial and error, or a variety of other calculations and/or experiments.

Once a desired sterility assurance level has been achieved, the ethylene oxide solution is removed from the sterilization chamber, and the device or assembly is aerated (1130) until it is safe for handling and distribution. Aeration may be achieved by a series of vacuums and subsequent injections of nitrogen gas into an aeration chamber, by for example, circulating filtered air through an aeration chamber, by circulating heated air through an aeration chamber, or based on a variety of other aeration techniques or combinations thereof. In other embodiments, exposure temperatures at, above, or below 56° C. and/or exposure humidity levels at, above, or below 35% may be used. In further embodiments, the EO exposure time and/or the EO concentration may vary.

Figure 12:
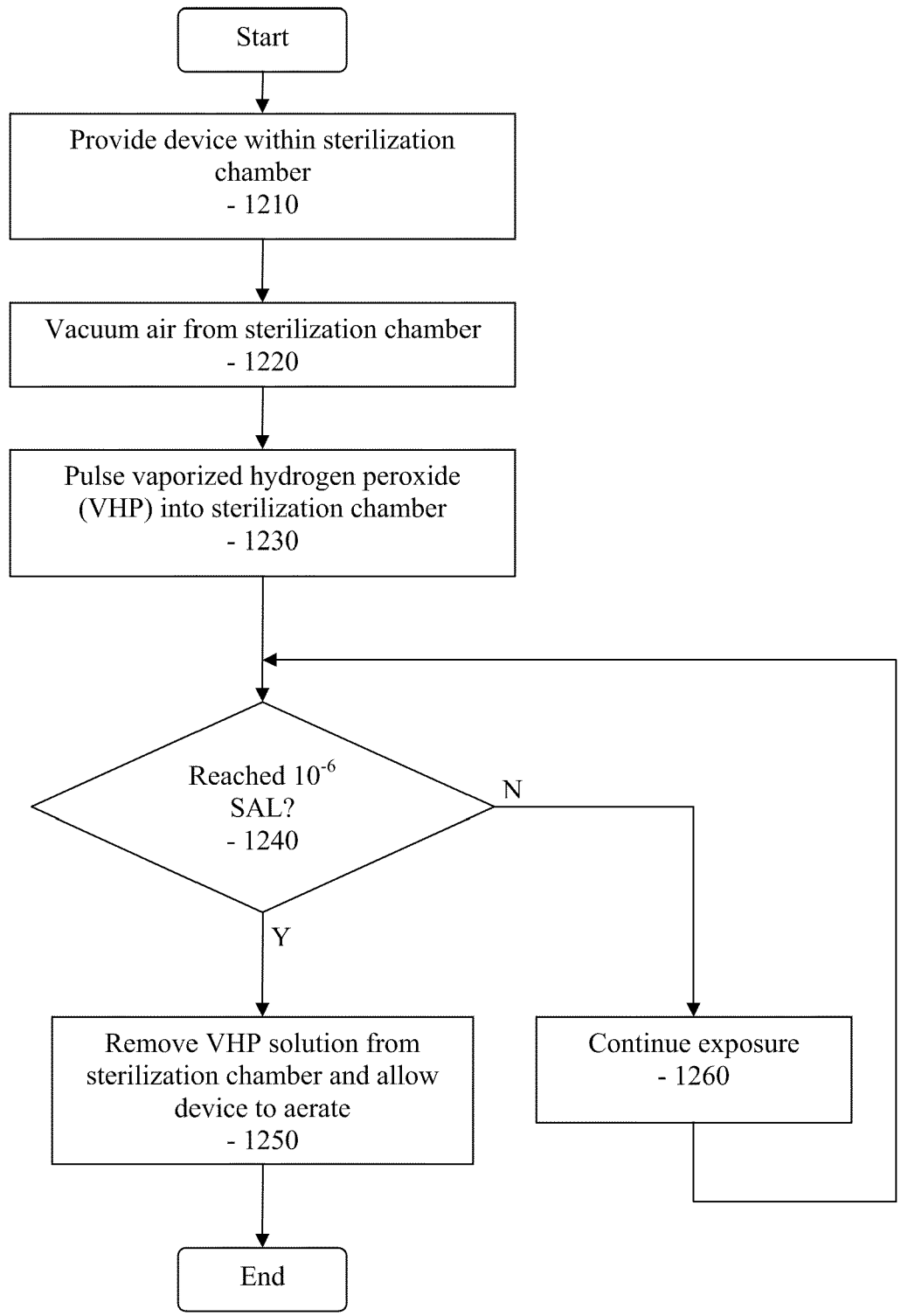
FIG. 12 is a flow chart illustrating a vaporized hydrogen peroxide based sterilization process in one aspect of the present disclosure.

FIG. 12 is a flow chart illustrating a vaporized hydrogen peroxide (VHP) based sterilization routine in one aspect of the present disclosure. Hydrogen peroxide is bactericidal, fungicidal, and sporicidal at concentrations above approximately 6%. In one embodiment, a hydrogen peroxide concentration between 20% and 50%, such as approximately 35%, may be used in VHP based sterilization routine.

Referring to FIG. 12, in one embodiment, the medical device assembly is provided within a sterilization chamber (1210), which is pulled by vacuum (1220) to ensure there are no leaks. Following the vacuum, the VHP is then pulsed into the sterilization chamber (1230), to permeate the VHP through the packaging and sterilize the sensor in the assembly while without damaging other components such as the electronics within the assembly. In one aspect, the VHP exposure is maintained (1260) until an acceptable sterility assurance level, such as $10^{-6}$ SAL, is achieved (1240). This cycle can be completed in minutes, or hours, or more or less and may be at temperatures ranging from approximately 30° C. to 40° C. and at low humidity levels, where humidity arises from the pulsed VHP injection. Various other combinations of temperature, humidity levels, VHP concentration, and exposure time may be used. High concentrations of hydrogen peroxide may be potentially dangerous or harmful to enzymes of a sensor, however, at low concentration it is not harmful. Once a desired sterility assurance level has been achieved, the hydrogen peroxide solution is removed from the sterilization chamber, and the device or assembly is aerated (1250) until it is safe for handling and distribution.

Figure 13:
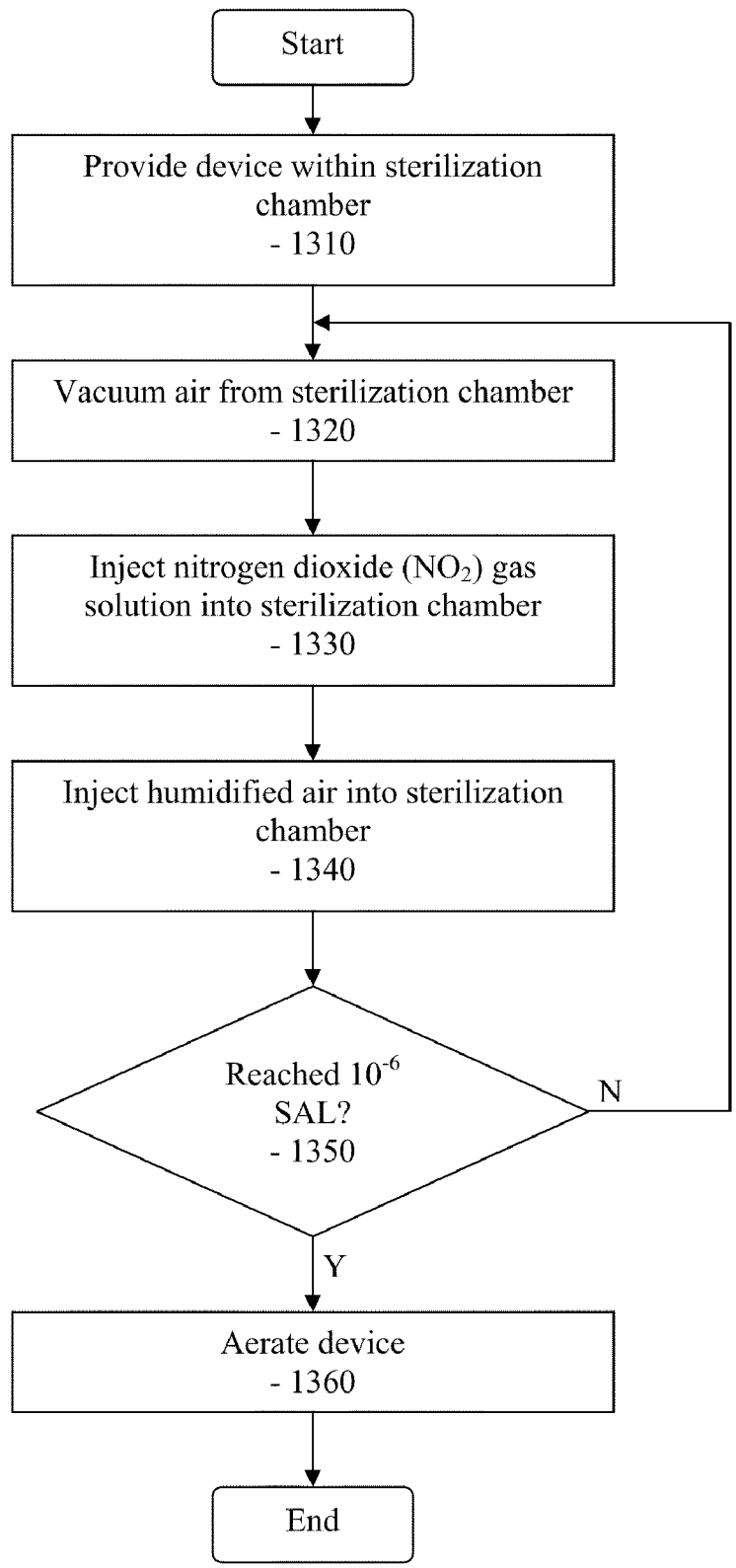
FIG. 13 is a flow chart illustrating a nitrogen dioxide based sterilization process in one aspect of the present disclosure.

FIG. 13 is a flow chart illustrating a nitrogen dioxide ($NO_2$) based sterilization routine in one aspect of the present disclosure. Referring to FIG. 13, in one embodiment, the $NO_2$ based sterilization routine uses low concentrations (less than approximately 21 mg/L) of $NO_2$ gas in the presence of air and water vapor at approximately room temperature delivered (1330) into a sterilization chamber that contains the device or assembly to be sterilized (1310) and that has been evacuated of air by the use of a vacuum (1320). In one aspect, the injection of the $NO_2$ mixture is followed by an injection of humidified air (1340) at near ambient pressure into the sterilization chamber. In one aspect, this process is repeated one or more times until an acceptable sterility assurance level, such as $10^{-6}$ SAL, is achieved (1350). Once an acceptable SAL is achieved, the medical device assembly is aerated (1360) until it is safe for use and/or distribution.

In one embodiment, the $NO_2$ gas concentration used for sterilization is between approximately 8 mg/L and 10 mg/L. In another embodiment, the $NO_2$ gas to air ratio is between about 0.1% and 1%, such as between about 0.25% and 0.40%. In one embodiment, the exposure time is between one minute and one hour, such as between approximately two minutes and twenty minutes. In a further embodiment, the humidity level is between 35% and 90%, such as between 50% and 80%. In still another embodiment, the temperature is between 10° C. and 40° C., such as between 18° C. and 30° C. In still other embodiments, the concentration of $NO_2$, temperature, humidity, pressure, exposure time, number of exposure cycles, or combinations thereof may vary.

Within the scope of the present disclosure, other methods of chemical sterilization may be used including the use of gaseous or liquid chemicals including, chlorine bleach, glutaraldehyde, formaldehyde, Ortho-phthalaldehyde (OPA), peracetic acid, guanidinium thiocyanate, sodium hydroxide (NaOH), silver ions, iodine, ozone, hydrogen peroxide gas plasma, or combinations or derivatives thereof.

In other embodiments, a pre-assembled medical device assembly may include a component, for example a sensor which requires sterilization before distribution and use and protection from future contamination, may be incorporated within a housing of another component, such as the device assembly as shown in FIG. 6. As described above, it may be advantageous for a medical device assembly to be sterilized after complete assembly and packaging to avoid possible contamination between the sterilization process and the finalization processes of manufacture and assembly. As such, it is advantageous to provide a suitable material and/or design to allow for sterilization of all necessary components of the medical device assembly without sacrificing protection.

In one embodiment, a protective component (not shown), such as a cap, may be provided over the open end of the sensor delivery unit 600 of FIG. 6. Example embodiments are described in further detail in U.S. Provisional Application No. 61/149,639 filed Feb. 3, 2009, entitled "Compact On-Body Physiological Monitoring Device and Methods Thereof", disclosure of which is incorporated herein by reference for all purposes. In one aspect, the cap acts as a desiccation barrier, protecting the sensor 620 from potentially harmful outside elements. However, in some cases, a desiccation barrier may also hinder some sterilization processes, such as chemical sterilization methods, examples of which are described above.

Figure 14:
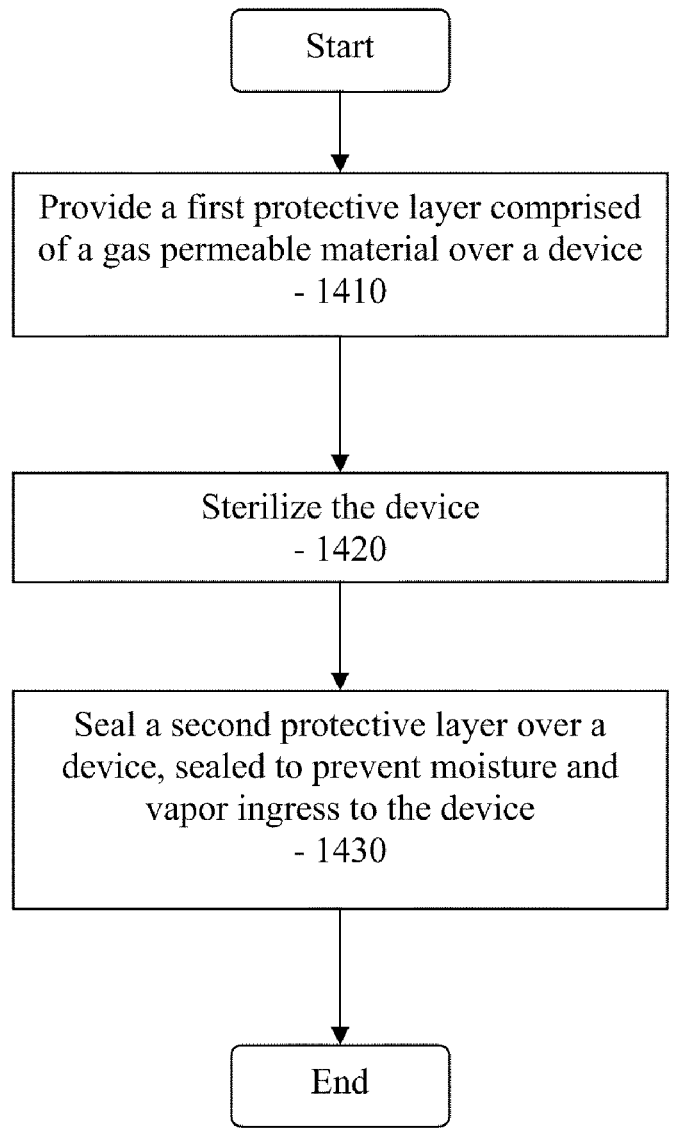
FIG. 14 is a flow chart illustrating a method of providing a protective component for a device in one aspect of the present disclosure.

In view of the above, FIG. 14 is a flow chart illustrating a method of providing a protective component for a device in one embodiment, wherein the protective component may be comprised of two or more layers of different materials. The first layer may be made of a synthetic material such a flash-spun high-density polyethylene fiber, such as DuPont™ Tyvek®, which is highly durable and puncture resistant and allows the permeation of vapors (1410). The Tyvek® is applied as the first layer of the protective component, before the sterilization process. Once the Tyvek® layer is applied, the medical device assembly is sterilized (1420), and following the sterilization process, a foil, or other vapor and moisture resistant material, layer is sealed, for example heat sealed, over the Tyvek® layer to prevent moisture ingress into the medical device assembly (1430).

In another embodiment, only a single protective layer is applied to the medical device assembly, wherein the single layer is gas permeable for the sterilization process, but is also capable of protection against moisture and other harmful elements once the sterilization process is complete.

In other embodiments, as described above, it may be advantageous for a medical device assembly to be packaged in final packaging materials before sterilization in order to avoid contamination between the sterilization and final packaging processes. In one embodiment, a packaging, for example a Tyvek® packaging, may be sealed around the medical device assembly. The entire sealed packaging is then sterilized before final shipping and distribution. In another embodiment, the sterilization process is completed before the final packaging is sealed, and immediately following the sterilization process the final packaging is sealed, for example, but heat sealing. In other embodiments, multiple layers and/or multiple materials of packaging may be used.

In still a further embodiment, separate components may be sterilized separately using different or the same sterilization techniques as described above, and assembled and packaged after sterilization. In another embodiment, some components may be sterilized individually before assembly and packaging, while the remaining components may be sterilized after assembly and/or packaging. In still another embodiment, each separate component may be sterilized separately before assembly and/or packaging, and further the entire assembled device may be sterilized an additional time after complete assembly and/or final packaging.

Within the scope of the present disclosure, other methods of sterilization of an analyte sensor or analyte sensor delivery unit may be used, including, but not limited to, radiation sterilization methods such as gamma ray irradiation, X-ray irradiation, or ultraviolet light (UV) irradiation, dry heat sterilization, and autoclaving sterilization. Gamma ray irradiation is similar to electron beam irradiation in that it penetrates most material and doesn't require long exposure. Gamma ray irradiation sterilization uses gamma rays which are generally produced from a Cobalt ($Co_{60}$) source. Gamma rays generally have a higher penetrating power compared to electron beam irradiation, however, they have a lower dosage rate. Therefore, gamma ray irradiation may be preferable for high density packaged materials, however, because of the lower dosage rate, the materials may require a longer dosage time to ensure full sterilization, and therefore, increase the risk of damage to the material itself from prolonged exposure.

X-ray irradiation, if low energy, is less penetrating than electron beam and gamma ray irradiation and thus often requires longer exposure time, but requires less shielding. Ultraviolet light irradiation may be ineffective in penetrating non-transparent materials, thus UV irradiation is used only for surface sterilization or sterilization of certain transparent objects.

Dry heat sterilization is a matter of heating the target package, device, or material to a desired sterilization heat level. However, dry heat often encounters problems when sterilizing plastics, as plastics may melt or damage before the entirety of the package, material, or device reaches a temperature adequate for sterilization.

Autoclaving is a sterilization process that uses saturated steam to allow for lower temperatures and shorter times as compared to the dry heat process. However, some materials begin to loose structural integrity at the temperatures used for autoclaving. This limits the materials and designs available for packaging a device.

In yet another embodiment of the present disclosure, a sterilization verification procedure may be implemented after sterilization. After sterilization, a sample may be taken for final quality control testing, which may check, among others, device, such as a sensor, response, pack integrity, such as leak testing, and device functionality, such as insertion functionality for an analyte sensor delivery unit.

As discussed above, sterilization of medical devices before usage is important. In one aspect, electron beam irradiation may be used for the sterilization of a medical device such as the sensor insertion unit and sensor combined assembly. The electron beam irradiation inactivates or kills any microorganisms on or within the target medical device by using electron beam accelerators to accelerate electrons into a concentrated highly charged electron stream, which may alter chemical and biological bonds of, for example, DNA chains and reproductive cells of microorganisms. Moreover, as discussed above, electron beam irradiation may be a penetrating process, allowing a target medical device, such as an analyte sensor and analyte sensor delivery unit, to be already packaged in its final packaging before being exposed to the irradiation process for sterilization.

Accordingly, in accordance with the embodiments of the present disclosure, there are provided methods and systems for the sterilization of medical devices, including devices for the continuous or automatic monitoring of analytes, such as glucose, in bodily fluid. In one aspect, there is provided assembling an analyte sensor with an analyte sensor insertion device, packaging the assembled analyte sensor and sensor insertion device in a container which may optionally include substantially airtight seal, and irradiating the packaged assembled analyte sensor and sensor insertion device at a dose effective to sterilize the package using one or more electron beam accelerators.

In one aspect, the electron beam sterilization of the assembled and packaged analyte sensor and sensor insertion device results in a relatively long term shelf life (for example, approximately 18 months), with controllable moisture content within the packaging, while not adversely impacting the adhesiveness of the adhesive for placement on the skin surface of the user.

Accordingly, a method of sensor delivery assembly sterilization in one aspect includes assembling an analyte sensor with an analyte sensor insertion device, packaging the assembled analyte sensor and sensor insertion device in a container, and irradiating the container including packaged assembled analyte sensor and sensor insertion device at a predetermined dose using one or more electron beam accelerators.

The predetermined dose may be approximately 30 kGy.

The packaged assembled analyte sensor and sensor insertion device may be irradiated at a surface dosage of between approximately 25 kGy and 60 kGy.

In one aspect, the irradiation of the packaged assembled analyte sensor and sensor insertion device may produce approximately $10^{-6}$ sterility assurance level.

The packaged assembled analyte sensor and sensor insertion device may be irradiated from two opposing sides using at least two electron beam accelerators, where, a respective time period associated with the irradiation of the packaged assembled analyte sensor and sensor insertion device from each of the at least two electron beam accelerators may be substantially non-overlapping.

The packaged assembled analyte sensor and sensor insertion device may be sterilized with one electron beam accelerator.

In still another aspect, the method may include rotating the container including packaged assembled analyte sensor and sensor insertion device during irradiation to expose the maximum surface of the packaged assembled analyte sensor and sensor insertion device substantially perpendicular to the electron beam irradiation.

The method may include providing an indication of sterilization status on the irradiated packaged assembled analyte sensor and sensor insertion device, where providing the indication of sterilization status may include affixing a label on the packaged assembled analyte sensor and sensor insertion device.

In yet another aspect, assembling the analyte sensor with the analyte sensor insertion device may include coupling the analyte sensor to the analyte sensor insertion device, where coupling may include detachably coupling the analyte sensor to a predetermined portion of the analyte sensor insertion device.

A system for sterilizing an analyte sensor insertion device assembly in another aspect of the present disclosure includes a container including an inner cavity and a seal, the container including an analyte sensor insertion device assembly positioned substantially within the inner cavity, wherein the seal is provided entirely over the cavity on the container, and an electron beam accelerator configured to irradiate the container at a predetermined dose.

The electron beam accelerator may be configured to irradiate the container at a surface dosage of between approximately 25 kGy and 60 kGy.

The electron beam accelerator irradiation of the container may result in approximately $10^{-6}$ sterility assurance level.

In one aspect, the analyte sensor includes a glucose sensor.

The container in a further aspect may include a sterilization status indicator. A method in still another aspect may include exposing a packaged assembly including an analyte sensor and sensor insertion device to electron beam irradiation to result in approximately $10^{-6}$ sterility assurance level.

In one aspect, the sealed analyte sensor and sensor delivery unit in a single package may be electron beam sterilized for a predetermined time period to attain sufficient level of sterilization (for example, approximately $10^{-6}$ sterility assurance level) while maintaining the integrity of the components and items within the package including, for example in certain embodiments, the active sensing agents and/or chemistry related to analyte sensing disposed on the sensor, the biologics and the required biological activity thereof, the viscosity of the adhesive on the bottom surface of the mounting unit of the sensor delivery unit, as well as the structural integrity of the sensor delivery unit components including, for example in certain embodiments, a metal sharp/introducer, a plastic housing, as well as other materials if included.

Embodiments include effectively electron beam sterilizing a medical device that includes various materials with respective material, biologic and chemical properties. Embodiments include exposing a medical device to electron beam irradiation for a period of time sufficient to sterilize the device without adversely affecting the properties of the assembled device (and any other component sterilized therewith) to an unacceptable degree. Sterilization may include determining that an electron beam-sterilized medical device is substantially, if not completely, free of viable microorganisms, e.g., does not exceed about an amount acceptable for such devices according to a governmental regulatory agency such as the U.S. Food and Drug Administration and/or the target medical device for sterilization has reached a predetermined sterility assurance level (SAL).

For example, a medical device subjected to the sterilization procedures herein may include an analyte sensor (such as a glucose sensor) that may include one or more electrodes (one or more of, including any combination of working, reference and counter electrodes), an analyte-responsive enzyme area (e.g., glucose enzyme with or without a mediator, e.g., a redox polymer enzyme area (such as an osmium-containing redox polymer)), or an analyte diffusion limiting area respectively disposed on the sensor substrate. An assembled unit that may be sterilized with an analyte sensor may include a mounting unit and/or a sensor delivery unit, comprising the target medical device for sterilization.

A mounting unit may include materials such as plastic (e.g., substantially flexible or substantially rigid plastic) and/or adhesive material disposed on one or more surface of the mounting unit (e.g., to adhere the mounting unit to a skin surface of a user). A sensor delivery unit may include materials such as plastic housing and one or more components (e.g., substantially flexible or substantially rigid plastic), and metal (such as a sharp or introducer for delivering a sensor at least partially in the skin of a user). Such an assembly comprising analyte sensor and mounting unit and sensor delivery unit may be positioned inside a container prior to sterilization, where a container may also include one or more materials whose properties may be considered in the sterilization process for example, to achieve the desired sterility assurance level.

In one aspect, the container materials may include a thermoformed plastic tray with a sealable, removable cover, e.g., an aluminum foil cover that is adhered to the plastic tray with adhesive. In one embodiment, the thermoformed plastic tray for containing the assembled analyte sensor, pre-loaded in the sensor delivery unit configured with the mounting unit, may comprise a composition including polyester terephthalate glycol (PETG)/Cyclic Olefine Copolymer (COC)/polyester terephthalate glycol (PETG) of an approximate thickness of 40 millimeters. Additionally, the removable cover may be provided on the thermoformed plastic tray as peelable lid which is adhered to the plastic tray using an adhesive, and may be peeled off by a user prior to use. In particular embodiments, the peelable lid may be a composition including polyester/white polyethylene/aluminum foil/polyester/heat seal PET film. In certain aspects, the adhesively mounted lid or cover may be flexible or rigid. When fully assembled, the container including the plastic tray and the aluminum foil cover provides a sealed environment for the assembled sensor, sensor delivery unit and/or the mounting unit.

Once positioned inside, the cover may be sealed to form an enclosed interior space. In certain embodiments, sterilization of a medical device having various materials, by a process herein, provides sterility of the medical device for a predetermined shelf life period of time, e.g., at least about six months, e.g., at least about 18 months.

In one aspect, the period of time during which the sensor/delivery unit is exposed to the electron beam irradiation may vary, but in certain embodiments may range from at least about one minute, e.g., at least about one to two minutes, e.g., at least about two minutes, where the period of time may be as long as about three minutes or longer. Furthermore, in one aspect, the target surface dose for electron beam sterilization is within a rage of 25 kGy to 60 kGy, and preferably, about 29 or 30 kGy target surface dose to maintain a minimum of approximately 25 kGy within the interior of the packaging.

In certain embodiments, the electron beam sterilization of the packaged sensor and sensor delivery unit is performed to meet the standards or are in compliance with the requirements set forth in ISO 11137 which provides the requirements for validation and routine control for radiation sterilization of health care products, and AAMI TIR27: 2001 Sterilization of health care products—Radiation sterilization—Substantiation of 25 kGy as a sterilization dose Method $VD_{MAX}$.

Within the scope of the present disclosure, the time period of the electron beam irradiation and the target surface dosage mage vary depending upon the particular item or combination of components for sterilization. For example, the target surface dose and irradiation time period for a packaging that includes analyte sensor only may differ from a packaging that includes the sensor delivery unit and the analyte sensor pre-loaded in the delivery unit, and further which includes the mounting base for positioning on the user's skin surface during the sensor insertion process. In particular, the target surface dose and/or irradiation time period may be varied to compensate for the particular material properties of the item for sterilization.

In one embodiment, a method of sterilizing a medical device assembly may comprise providing a medical device assembly including one or more electronic components, a sensor, and a sensor delivery unit, exposing the medical device assembly to a gaseous chemical solution at a predetermined temperature, humidity level, and gaseous chemical concentration, for a predetermined exposure time to sterilize the medical device assembly, and aerating the medical device assembly.

The electronic components may include a data transmitter, a microprocessor, or a memory device.

The sensor may be a glucose sensor.

In one aspect, the glucose sensor may comprise at least one electrode, an enzyme area, and a glucose diffusion limiting area.

The enzyme area may comprise a mediator.

The enzyme area may comprise a redox polymer.

The redox polymer may comprise an osmium-containing polymer.

The glucose diffusion limiting area may comprise a polymer.

The sensor may comprise a substantially planar substrate on which the at least one electrode is positioned.

The sensor delivery unit may include an adhesive mounting unit.

In one aspect, the gaseous chemical solution is an ethylene oxide solution.

The predetermined ethylene oxide concentration may be between 400 mg/L and 800 mg/L.

The predetermined ethylene oxide concentration may be approximately 600 mg/L.

The exposure time may be between three and five hours.

The predetermined temperature may be lower than 56° C.

The predetermined temperature may be approximately 45° C.

The predetermined humidity level may be approximately 35%.

In another aspect, the gaseous chemical solution may be a vaporized hydrogen peroxide solution.

The predetermined vaporized hydrogen peroxide concentration may be approximately 35%.

The predetermined temperature may be between 30° C. and 40° C.

In another aspect, the gaseous chemical solution may be an oxide of nitrogen solution.

The oxide of nitrogen may be nitrogen dioxide.

The nitrogen dioxide concentration may be between 0.25% and 0.40%.

The exposure time may be between 2 and 20 minutes.

The predetermined temperature may be between 18° C. and 30° C.

The predetermined humidity may be between 50% and 80%.

In yet another aspect, the medical device assembly may be sterilized when the medical device has a $10^{-6}$ sterility assurance level.

The medical device assembly may be sterilized to maintain a predetermined sterility level for at least about six months.

The medical device assembly may be sterilized to maintain a predetermined sterility level for at least about 18 months.

The medical device assembly may be provided within a final packaging prior to exposure to the gaseous chemical solution.

Furthermore, the method may comprise packaging the medical device assembly in a material that is substantially non-permeable to moisture.

Packing the medical device assembly may comprise heat sealing the medical device assembly within the material that is substantially non-permeable to moisture.

Various other modifications and alterations in the structure and method of operation of this disclosure will be apparent to those skilled in the art without departing from the scope and spirit of the present disclosure. Although the present disclosure has been described in connection with specific embodiments, it should be understood that the present disclosure as claimed should not be unduly limited to such specific embodiments. It is intended that the following claims define the scope of the present disclosure and that structures and methods within the scope of these claims and their equivalents be covered thereby.

What is claimed is:

1. A method of sterilizing a glucose sensor assembly, the method comprising:
    assembling a glucose sensor with a sensor mounting unit and a sensor delivery unit, where the glucose sensor comprises at least one electrode, an enzyme area, and a glucose diffusion limiting area, the sensor delivery unit comprises a housing and a metal sharp, and the sensor mounting unit comprises an adhesive;
    irradiating the assembly with a predetermined dose level and/or for a predetermined time period to sterilize the assembly;
    packaging the assembly in a first container;
    packaging the first container in a second container that includes a predetermined number of packaged assemblies; and
    irradiating the second container including packaged assemblies at a predetermined dose using one or more electron beam accelerators.

2. The method of claim 1, comprising positioning the assembly in a container and sealing the assembly in the container with a cover.

3. The method of claim 2 wherein the container includes thermoformed plastic.

4. The method of claim 2 wherein the cover includes aluminum.

5. The method of claim 2 wherein the cover and the container form the seal with an adhesive material disposed therebetween.

6. The method of claim 1 wherein the assembly is irradiated at a surface dosage of between approximately 25 kGy and 60 kGy.

7. The method of claim 1 wherein the irradiation of the packaged assembled analyte sensor and sensor insertion device results in about $10^{-6}$ sterility assurance level.

8. The method of claim 1 wherein the assembly is sterilized to maintain a predetermined sterility level for at least about six months.

9. The method of claim 1 wherein the assembly is sterilized to maintain a predetermined sterility level for at least about 18 months.

10. The method of claim 1 wherein the enzyme area comprises a mediator.

11. The method of claim 10, wherein the enzyme area comprises a redox polymer.

12. The method of claim 11 wherein the redox polymer comprises an osmium-containing polymer.

13. The method of claim 1 wherein the glucose diffusion limiting area comprises a polymer.

14. The method of claim 1 wherein the sensor comprises a substantially planar substrate on which the at least one electrode is positioned.

15. A method of sensor delivery assembly sterilization, comprising:
    assembling an analyte sensor with an analyte sensor insertion device;
    packaging the assembled analyte sensor and sensor insertion device in a first container;
    packaging the first container in a second container that includes a predetermined number of packaged assembled analyte sensors and sensor insertion devices; and
    irradiating the second container including packaged assembled analyte sensor and sensor insertion device at a predetermined dose using one or more electron beam accelerators.

16. The method of claim 15, wherein the predetermined dose is approximately 30 kGy.

17. The method of claim 15, wherein the packaged assembled analyte sensor and sensor insertion device are irradiated at a surface dosage of between approximately 25 kGy and 60 kGy.

18. The method of claim 15, wherein the irradiation of the packaged assembled analyte sensor and sensor insertion device produces about $10^{-6}$ sterility assurance level.

19. The method of claim 15, wherein the packaged assembled analyte sensor and sensor insertion device are irradiated from two opposing sides using at least two electron beam accelerators.

20. The method of claim 19, wherein a respective time period associated with the irradiation of the packaged assembled analyte sensor and sensor insertion device from each of the at least two electron beam accelerators are substantially non-overlapping.

21. The method of claim 19, wherein the irradiation of the packaged assembled analyte sensor and sensor insertion device produces about $10^{-6}$ sterility assurance level.

22. The method of claim 15, wherein the packaged assembled analyte sensor and sensor insertion device is sterilized with one electron beam accelerator.

23. The method of claim 22 including rotating the packaged assembled analyte sensor and sensor insertion device during irradiation to expose the maximum surface of the packaged assembled analyte sensor and sensor insertion device substantially perpendicular to the electron beam irradiation.

24. The method of claim 22, wherein the irradiation of the packaged assembled analyte sensor and sensor insertion device produces about $10^{-6}$ sterility assurance level.

25. The method of claim 15, including providing an indication of sterilization status on the irradiated packaged assembled analyte sensor and sensor insertion device.

26. The method of claim 15, wherein assembling the analyte sensor with the analyte sensor insertion device includes coupling the analyte sensor to the analyte sensor insertion device.

27. The method of claim 26 wherein coupling includes decoupleably coupling the analyte sensor to a predetermined portion of the analyte sensor insertion device.

28. A method, comprising:
packaging an assembled analyte sensor and sensor insertion device in a first container:
exposing the first container including the analyte sensor and the sensor insertion device to electron beam irradiation to result in approximately $10^{-6}$ sterility assurance level;
packaging the first container in a second container that includes a predetermined number of packaged assembled analyte sensors and sensor insertion devices; and
irradiating the second container including the predetermined number of packaged assembled analyte sensors and sensor insertion devices at a predetermined dose using one or more electron beam accelerators.

* * * * *

UNITED STATES PATENT AND TRADEMARK OFFICE
CERTIFICATE OF CORRECTION

PATENT NO. : 8,252,229 B2
APPLICATION NO. : 12/422223
DATED : August 28, 2012
INVENTOR(S) : Christopher Allen Thomas and Jasmin Y. Zhao It is certified that error appears in the above-identified patent and that said Letters Patent is hereby corrected as shown below:

Specification
Column 6, line 37, replace "HIPPA" with --HIPAA--.
Column 7, line 56, replace "trace" with --contact--.
Column 8, line 62, replace "section 104 can" with --section 309 can--.
Column 9, line 31, replace "unit 105, or" with --unit 106, or--.
Column 14, line 25, replace "sending layer" with --sensing layer--.
Column 19, line 50, replace "the case." with --the case 930.--.

Signed and Sealed this
Twenty-first Day of June, 2016

Michelle K. Lee
*Director of the United States Patent and Trademark Office*